United States Patent [19]

Johnson et al.

[11] Patent Number: 5,038,852
[45] Date of Patent: Aug. 13, 1991

[54] APPARATUS AND METHOD FOR PERFORMING AUTOMATED AMPLIFICATION OF NUCLEIC ACID SEQUENCES AND ASSAYS USING HEATING AND COOLING STEPS

[75] Inventors: Larry J. Johnson, San Jose; Joseph T. Widunas, Berkeley, both of Calif.

[73] Assignee: Cetus Corporation, Emeryville, Calif.

[21] Appl. No.: 494,174

[22] Filed: Mar. 14, 1990

Related U.S. Application Data

[60] Division of Ser. No. 899,061, Aug. 22, 1986, which is a continuation-in-part of Ser. No. 833,368, Feb. 25, 1986.

[51] Int. Cl.⁵ .................. F23N 5/20; G01N 35/02
[52] U.S. Cl. .................. 165/12; 73/863.11; 236/46 R; 422/116; 436/50
[58] Field of Search .......... 165/12; 236/46 R; 364/557; 73/863.11; 422/116; 436/50

[56] References Cited

U.S. PATENT DOCUMENTS

| | | | |
|---|---|---|---|
| 3,311,303 | 3/1967 | Noyes | 236/46 R |
| 3,392,914 | 7/1968 | Nienstaedt | 236/46 R |
| 3,856,471 | 12/1974 | Winitz et al. | |
| 3,912,913 | 10/1975 | Bunting | 236/46 P X |
| 3,983,363 | 9/1986 | Alter | 219/521 |
| 4,008,048 | 2/1977 | Hellmans et al. | 137/209 X |
| 4,206,872 | 6/1980 | Levine | 236/46 R |
| 4,312,835 | 1/1982 | Zoltan et al. | 422/70 |
| 4,335,620 | 6/1982 | Adams | 73/863.11 |
| 4,362,699 | 12/1982 | Verlander et al. | 422/131 |
| 4,404,845 | 9/1983 | Schrenker | 73/61.1 |
| 4,474,015 | 10/1984 | Christmas et al. | 62/3 |
| 4,478,094 | 10/1984 | Salomaa et al. | 73/864.14 |
| 4,483,823 | 11/1984 | Umetsu et al. | 422/63 |
| 4,504,733 | 3/1985 | Walsh | 219/521 |
| 4,517,160 | 5/1985 | Galle et al. | 422/65 |
| 4,518,700 | 5/1985 | Stephens | 436/52 |
| 4,534,941 | 8/1985 | Stephens et al. | 422/70 |
| 4,544,436 | 11/1985 | Chlosta et al. | 219/385 |
| 4,598,049 | 7/1986 | Zelinka et al. | 435/287 |
| 4,683,194 | 7/1987 | Saiki et al. | 435/6 |
| 4,685,081 | 8/1987 | Richman | 365/1 |
| 4,708,886 | 11/1987 | Nelson | 422/63 |
| 4,711,851 | 12/1987 | McNamara et al. | 435/287 |

FOREIGN PATENT DOCUMENTS

| | | |
|---|---|---|
| 171140 | 5/1984 | European Pat. Off. |
| 2650593 | 5/1977 | Fed. Rep. of Germany |
| 2413708 | 12/1977 | France |
| 2161815 | 1/1986 | United Kingdom |

OTHER PUBLICATIONS

Histomat advertisement, R. Jung GmbH, Oct., 1980.
Techne Brochure for Temperature programmer TP-16, Dec., 1984.
Forma Scientific Advertisement, Analytic Chemisty, Aug. 8, 1982.
Cole-Parmer Instrument Co., 1985-86 Catalog (complied 1984).
Lake Shore Cryotronics, Inc., Review of Scientific Instruments, Jul. 1980.
Barber-Colman Co., 1980.
Techne Brochure, 6/1982.
Techne Ad for Dri Block PHC-1.

(List continued on next page.)

*Primary Examiner*—William E. Wayner
*Attorney, Agent, or Firm*—Ronald C. Fish; Kevin R. Kaster

[57] ABSTRACT

There is disclosed herein a machine for performing nucleic acid amplification under computer control. The machine utilizes any one of a number of heating and cooling systems under control of a host computer which directs the heating and cooling systems to heat and cool a reaction-chamber-containing heat exchanger at appropriate times in the process. The reaction chambers are pre-loaded with the nucleic acid(s) to be amplified, a thermostable enzyme to catalyze polymerization, specific oligonucleotide primers, and four different nucleotide triphosphates. Also disclosed is the process for the amplification chain reaction implemented by the machine, which utilizes a thermostable enzyme.

4 Claims, 9 Drawing Sheets

OTHER PUBLICATIONS

Techne TP-16 Temperature Programmer Advertisement.
Biores b.v. Bioexcellence TAQ-Polymerase and Ampliclone Kit Ad.
Techne PHC-2 Ad.
Techne PCH-2 Temperature Cycler Ad.
Techne Flow Coolers FC-200 and FC200 and Dip Cooler RU-200.
Techne Tempunit or Tempette Immersion Circulators Ad.
Dialog Search for Techne Patents.
Brookfield Test Chamber.
Cole-Parmer Instr. Co. 1985-86 Catalog.
IEEE Transactions on Biomedical Engineering, vol. BME-29, No. 8, Aug. 1982, pp. 557-568 V. J. Anselmo, et al. "Programmable Temperature Control System for Biological Materials".
"Amino Acid Analysis System" Rev. Sci. Instrum. 51(7), Jul. 1980.
"Advances in Laboratory Automation Robotics 1984" by Zynark Corp.
"Studies on Polynucleotides—The Linkage of Deoxyribopolynucleotide Templates to Cellulose and Its Use in Their Replication" by Panet and Khorara, The Journal of Biological Chemistry, vol. 249, No. 16, issue of Aug. 25, pp. 5213-5221 (1974).
"Studies on Polynucleotides—Repair Replication of Short Synthetid DNA's as Catalyzed by DNA Polymerase" by Kleppe, et al., J. Mol. Biol. (1971) 56, pp. 341-461.
"Studies on Polynucleotides—Total Synthesis of the Structural Gene for an Alanic Transfer Ribonucleic Acid from Yeast", by Khorana et al., J. Mol. Biol. (1972) 72, pp. 209-217.
"Studies on Polynucleotides—Hybridization of Polydeoxynucleotides with Tyrosine Transfer RNA Sequences to the $p$-Strand of $\phi$80 psu DNA", by Miller et al., J. Mol. Biol. (1972) 72, pp. 503-522.
Automation of Microliter Plate Chromogenic Substrate Lal Endotoxin Assay Method by Use of a Modified Pro/Pette Express System, Martin et al., J. Parent Sci. Tech. vol. 40, No. 2, pp. 61-66, Mar. -Apr., 1986.
Saiki et al., "Enzymatic Amplification of B-Globin Genomic Sequences and Restriction Site Analysis for Diagnosis of Sickle Cell Anemia", Science, vol. 320, pp. 1350-1354, Dec. 1985.
Tecam Dry Heat Baths, Catalog 7051081.
Techne (OG-1 Block Digestor), Catalog 7051091.
Techne (Dri-Block 08-3), Catalog 7051101.

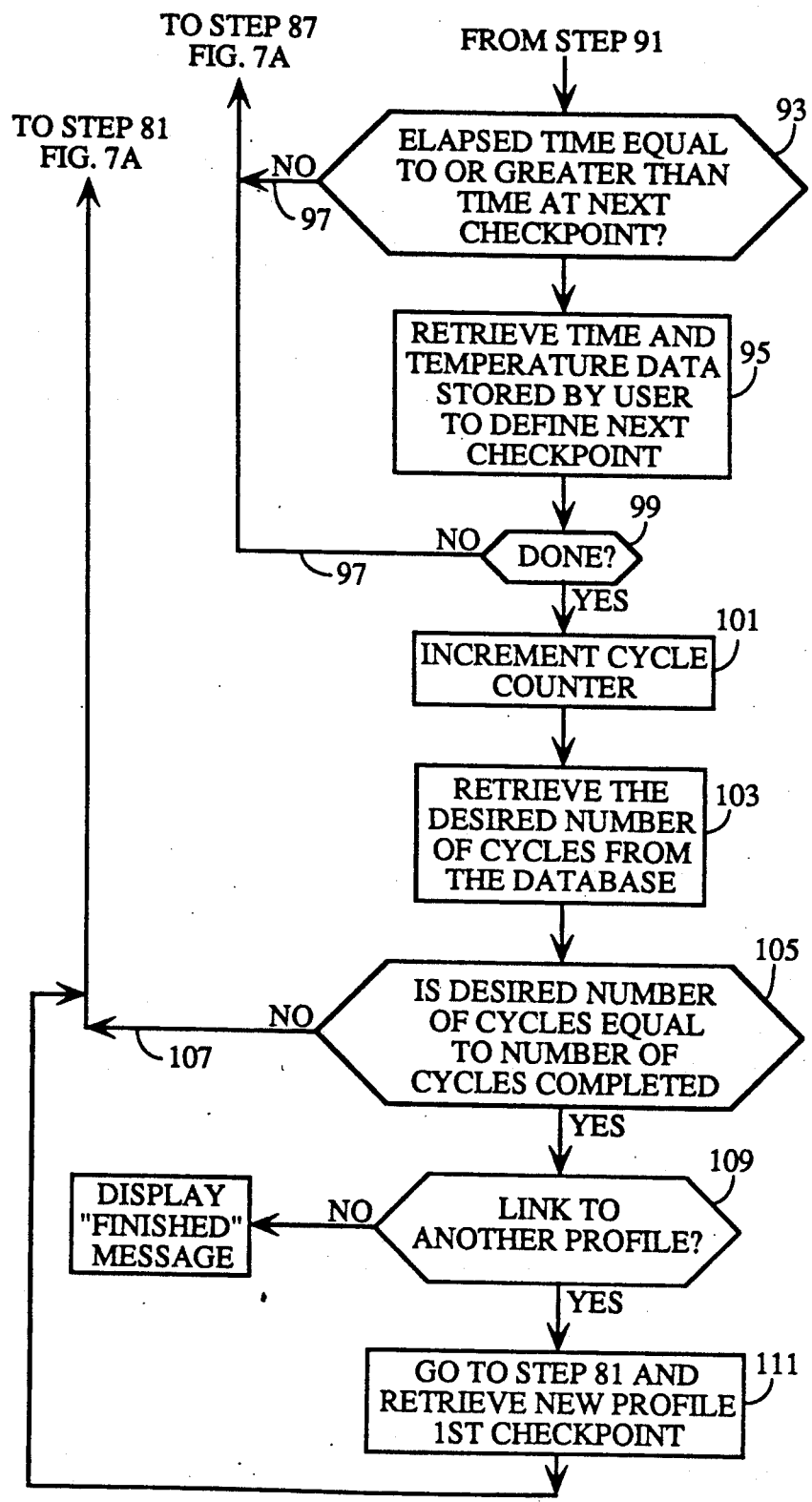

APPARATUS AND METHOD FOR PERFORMING AUTOMATED AMPLIFICATION OF NUCLEIC ACID SEQUENCES AND ASSAYS USING HEATING AND COOLING STEPS

This application is a division of 899,601, filed 8/22/86, which is a continuation-in-part application of copending U.S. patent application Ser. No. 833,368 (pending) filed Feb. 25, 1986, which is hereby incorporated by reference. This application is also related to copending U.S. patent application Ser. Nos. (Cetus docket Nos. 2262.1, 2303, and 2177.3), all filed concurrently herewith, Docket No. 2262.1 being a continuation-in-part application of copending U.S. application Ser. No. 839,331, filed Mar. 13, 1986, and Docket No. 2177.3 being a continuation-in-part application of copending U.S. application Ser. No. 828,144, filed Feb. 7, 1986, which is a continuation-in-part application of copending U.S. application Ser. No. 824,044, filed Jan. 30, 1986, which is a divisional application of copending U.S. application Ser. No. 791,308, filed Oct. 25, 1985, which is a continuation-in-part application of U.S. application Ser. No. 716,975 filed Mar. 28, 1985, now abandoned.

BACKGROUND OF THE INVENTION

The invention pertains to the field of chain reactions for amplifying DNA or RNA (nucleic acids), and, more particularly, to the field of machines for automatically performing this process through temperature cycling.

Methods described in the past for synthesizing nucleic acid sequences from an existing sequence, for example, the phosphodiester and phosphotriester methods [Narang et al., *Meth. Enzymol.* 68, 90 (1979); and Brown et al., *Meth. Enzymol.* 68, 109 (1979), respectively], are not practical to produce large amounts of nucleic acid sequences. Such methods are laborious and time-consuming, require expensive equipment and reagents, and have a low overall efficiency.

There are methods for producing nucleic acid sequences in large amounts from small amounts of an existing sequence. Such methods involve cloning of a nucleic acid sequence in an appropriate host system, and culturing the host, wherein the vector in which the nucleic acid sequence has been inserted is replicated, resulting in copies of the vector and hence the sequence. See T. Maniatis, et al., *Molecular Cloning: A Laboratory Manual,* Cold Spring Harbor Laboratory, pp. 390–401 (1982); and U.S. Pat. Nos. 4,416,988 and 4,403,036. The original sequence can also be organically synthesized before insertion in a vector. See U.S. Pat. No. 4,293,652.

A method, described by Saiki et al., *Science,* 230, 1530–1534 (1985), has been devised for amplifying one or more specific nucleic acid sequences or a mixture thereof using primers, nucleotide triphosphates, and an agent for polymerization, such as DNA polymerase. The extension product of one primer, when hybridized to the other, becomes a template for the production of the desired specific nucleic acid sequence, and vice versa. The process is repeated as often as necessary to produce the desired amount of the sequence.

This method is especially useful for performing clinical tests on the DNA or RNA from a fetus or other donor where large amounts of the DNA or RNA are not readily available and more DNA or RNA must be manufactured to have a sufficient amount to perform tests. The presence of diseases which have unique DNA or RNA signatures can be detected by amplifying a nucleic acid sample from a patient and using various probe procedures to assay for the presence of the nucleic acid sequence being detected in the test. Such test might be prenatal diagnosis of sickle cell anemia, as described by Saiki et al., supra, where the amplification of specific β-globin target sequences in genomic DNA resulted in the exponential increase (220,000 times) of target DNA copies, increasing sensitivity and speed while reducing the complexity of diagnosis. Another test is the diagnosis of the AIDS virus, which is thought to alter the nucleic acid sequence of its victims.

Five patent applications which describe the amplification process are copending U.S. patent application Ser. No. 818,127, filed Jan. 10, 1986, copending U.S. Ser. No. 716,982, filed Mar. 28, 1985, copending U.S. Ser. No. 791,308, filed Oct. 25, 1985, copending U.S. Ser. No. 828,144, filed Feb. 7, 1986, and copending U.S. Ser. No. 839,331, filed Mar. 13, 1986, the disclosures of all of which are incorporated herein by reference.

The amplification method bears some similarity to the molecular cloning methods described above, but does not involve propagation of a host organism, avoiding the hazards and inconvenience therein involved. In addition, the amplification method does not require synthesis of nucleic acid sequences unrelated to the desired sequence, and thereby obviates the need for extensive purification of the product from a complicated biological mixture. Finally, the amplification is more efficient than the alternative methods for producing large amounts of nucleic acid sequences from a target sequence and for producing such sequences in a comparatively short period of time.

At first, the amplification procedure described above was carried out by hand in the laboratories. The manual process involves a great deal of repetitive liquid handling steps and incubations at controlled temperatures. This is not only time-consuming and tedious, but it is also subject to error caused by human operator attention span drift. Such errors could result in a misdiagnosis of a genetic birth defect and an unnecessary abortion or the lack of an abortion where a birth defect exists. Further, such errors could result in misdiagnosis of sickle cell anemia or other genetic disorders.

Further, certain nucleic acids amplify more efficiently than others, so some nucleic acid sequence amplifications require more amplification cycles than others. Because the cost of laboratory labor can be high, and the risks to which a laboratory is subjected are high in case of error in erroneously performing amplification, there has arisen a need for a system which can automate the amplification process.

Such a machine is described in copending U.S. application Ser. No. 833,368 filed Feb. 25, 1986, which is the parent application of the present application. This machine utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence to be amplified plus certain reagents. The computer includes a user interface through which a user can enter process parameters which control the characteristics of the various steps in the sequence such as the times and temperatures of incubation, the amount of enzyme to transfer on each cycle into the second receptacle from the first receptacle, as well as the number of cycles through the amplification sequence that the user desires the machine to perform.

While the above-described machine increases the amount of nucleic acid sequence which can be amplified per unit of labor, thereby decreasing the possibility of error, it involves liquid handling, where reagents must be continuously transferred at various cycles. There is a need for a machine which not only automates the amplification process, but also makes it faster and more convenient. This can be accomplished using an enzyme which is thermostable, i.e., will not break down when subjected to heat.

SUMMARY OF THE INVENTION

This invention utilizes a temperature-cycling instrument for implementing the amplification process when a thermostable enzyme is employed. The use of a thermostable enzyme avoids the need for liquid transferring of the enzyme, which is necessitated when the enzyme is stable in the presence of heat.

More specifically, the invention herein relates to an apparatus for performing automated amplification of at least one specific nucleic acid sequence comprising:

a heat conducting container for holding a reaction mixture comprising a thermostable enzyme, said nucleic acid sequence(s) to be amplified, four different nucleotide triphosphates, and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer;

means for heating, cooling, and maintaining said container to or at any of a plurality of predetermined (user-defined) temperatures and having an input for receiving a control signal controlling which of said predetermined temperatures at or to which said container is heated, cooled, or maintained; and a computer means, coupled to the input of said means for heating and cooling to generate the proper control signals to control the temperature levels, temperature rate-of-change ramps, and timing of the incubations at certain temperature levels.

This invention also provides an apparatus for performing automated amplification of at least one specific nucleic acid sequence comprising:

a first means for holding a reaction mixture comprising said nucleic acid sequence(s) to be amplified, four different nucleotide triphosphates, a thermostable enzyme, and one oligonucleotide primer for each different specific sequence being amplified, wherein each primer is selected to be substantially complementary to different stands of each specific sequence, such that the extension product synthesized from one primer, when it is separated from its complement, can serve as a template for synthesis of the extension product of the other primer, said holding being carried out at any selected temperature or plurality of temperatures; and a second means for automatically performing a predetermined sequence of steps including causing said first means to heat its contents for a first period and to cool its contents for a second period.

In yet another embodiment, the invention herein provides an apparatus for performing an assay including heating and cooling steps as part of the sequence of steps of the assay comprising:

means for performing the sequence of steps wherein heating and cooling steps would be beneficial; and means in said means for performing for causing said heating and cooling steps to be performed at the proper point in the sequence of steps comprising the assay.

In another embodiment, this invention provides a method for amplifying at least one specific nucleic acid sequence comprising the steps of:

using a computer-directed machine to heat to a predetermined temperature for a predetermined time a sample of the nucleic acid sequence(s) to be amplified, four different nucleotide triphosphates, a thermostable enzyme, and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer (hereafter the mixture); and using a computer-directed machine to chill the mixture to a predetermined temperature.

In still another embodiment, this invention provides a method of amplifying at least one specific nucleic acid sequence comprising the steps of:

a) using a computer-directed machine to issue a heat signal to a heating apparatus to cause a reaction chamber to be heated for a predetermined time to and/or at a predetermined temperature, wherein said reaction chamber contains the mixture described above;

b) using a computer-directed machine to issue a cool signal to a cooling apparatus to cause said reaction chamber to be cooled for a predetermined time to and/or at a predetermined temperature; and c) using a computer-directed machine to repeat the cycle consisting of steps a through c when the elapsed time for the active cooling signal equals a user-defined time if the number of cycles performed thus far is less than a user-defined number of cycles.

The apparatus herein also generally contains a power supply for operation, a structural system to contain all the elements of the apparatus, and a keyboard and display panel to allow control of the apparatus by an operator.

The receptacle which holds the reagents where the reaction occurs has its temperature controlled by a computer to conform to a certain incubation profile defined by the user. Three circulating fluid reservoirs and solenoid operated valves, or any other method, may be employed to control temperature. The Peltier heat pumps available from Materials Electronics Products Corporation in Trenton, N.J. may also be used, as well as a water heat exchanger or any other heating and cooling system which may be controlled by a computer.

If solenoid-operated valves are employed, they are coupled to the computer such that the proper temperature fluid can be directed through the supported structure for the heat-conducting receptacle at the proper times in the amplification process under computer control. The receptacle is switched under computer control between two temperatures by the transmission of a control signal to the solenoid-operated valves at the proper time in the sequence to gate either the hot fluid or the cold fluid through the support structure of the receptacle. A temperature sensor coupled to the reaction chamber and the computer is used to provide a signal indicating the actual temperature. The computer compares the actual temperature to the desired temperature. An error signal is generated in this fashion which is used to control the apparatus which heats and cools the reaction chambers. The computer also keeps track of the elapsed time at particular temperatures to implement the incubation periods in the protocol.

The basic process that the machine performs to implement the amplification protocol after the starting materials are loaded into the reaction well, in one embodiment using water baths, is as follows.

The computer signals the solenoid-operated valves to gate the hot fluid through the supporting structure for the reaction chamber thereby heating the contents of the reaction well to the temperature of the hot fluid.

The amount of time the hot fluid is gated "on" is measured by an elapsed time counter.

The computer compares the elapsed time the hot fluid has been gated "on" to a variable set in memory. In the preferred embodiment, this variable can be changed by the user through the user interface. In other embodiments, it may be fixed.

When the elapsed time matches the variable for the hot incubation, the computer sends a signal to the solenoid-operated valves to stop the hot fluid flow and gate the cold fluid flow through the supporting structure for the reaction vessel.

In embodiments using temperature control feedback instead of empirically determined "on" times for the hot and cold fluids, a temperature profile versus time for the reaction chamber is programmed into the computer via the user interface. This causes the computer to control the reaction or reagent vessel temperature in the sequence required by the particular amplification reaction parameters. Such an embodiment uses a thermistor or other temperature sensor to monitor the temperature of the reaction chamber and generates an error signal derived by comparing the actual temperature of the reaction chamber to the user-defined temperature profile. The error signal is used to control a heat pump or other heating and cooling apparatus to maintain the desired temperature profile during the high temperature heat-up and high temperature incubation and during the chill-down and low-temperature incubation.

On either temperature feedback or empirically determined time embodiments, the computer starts a timer and compares the elapsed time for hot or cold fluid flow or the elapsed time at a particular temperature to a user-defined variable stored in memory for each segment or leg in the temperature profile. These variables can be set by the user in the preferred embodiment through the user interface. In embodiments where no temperature sensor is used, the variable for proposed time of hot or cold fluid flow is empirically determined by the user as the time it takes to heat or cool the reaction vessel to a predetermined temperature from the starting temperature plus the desired incubation time.

The above temperature profile control apparatus and methods for embodiments using hot and cold fluid reservoirs and solenoid-operated valves are equally applicable to embodiments using Peltier heat pumps or other forms of heating and cooling apparatus coupled to the reaction chamber or chambers.

DETAILED DESCRIPTION OF THE PREFERRED EMBODIMENTS

Amplification Machine Using Thermostable Enzyme and No Liquid Handling

Figure 1:
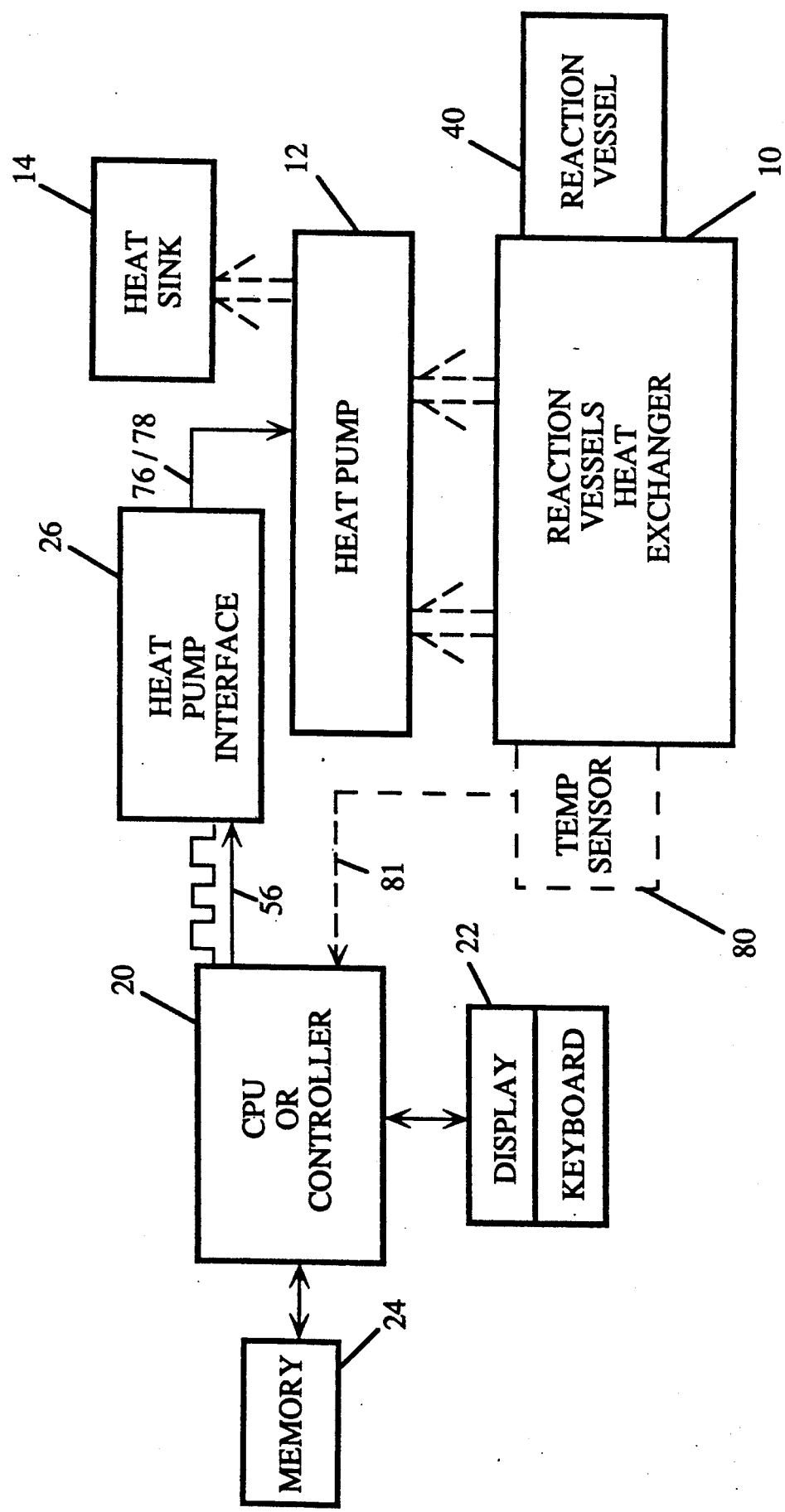
FIG. 1 is a general block diagram of a machine which can perform the amplification process using the thermostable enzyme and Peltier heat pumps to cycle the temperature of the reaction vessels.

Referring to FIG. 1, there is shown a general block diagram of a machine which can perform the nucleic acid amplification process using the thermostable enzyme. The starting materials, comprised of the nucleic acid samples to be amplified and the necessary reagents, are initially loaded into a reaction well 40 in heat exchanger 10. The heat exchanger 10 supports the reaction well 40, which may be a recess machined into the heat exchanger, but preferably is a plastic container which holds the fluids involved in the reaction and which sits in a recess formed in heat exchanger 10 (hereafter sometimes referred to as plate 1). In the preferred embodiment, heat exchanger 10 is a heat-conducting block, preferably aluminum, with a plurality of recesses formed therein sized to allow a given number of 0.5 ml (milliliter) Eppendorf tubes to fit therein.

The purpose of the tubes is to line the reaction well to separate the fluids from the walls of the recesses in the heat exchanger 10 to avoid cross contamination when the same reaction well is used to amplify different nucleic acid sequences. The purpose of heat exchanger 10 is to support the tubes and to act as a heat exchanger to transfer thermal energy to and from the fluids stored in the tubes in the reaction wells, such that the reaction components may be incubated at various temperatures for user-defined times.

To that end, heat exchanger 10 must be structured in such a way that the fluids in the reaction wells such as the reaction chamber 40 may be heated and cooled at the appropriate times in the process and for the appropriate duration. Any structure or method may be used to perform this heating and cooling function such as electrical heating and refrigeration apparatus in or connected to heat exchanger 10 such as a heat pump or Peltier or Thompson solid state thermoelectronic coolers. It is only necessary that whatever apparatus is used for this heating and cooling be capable of reaching and sustaining the temperatures involved, and that the apparatus for heating and cooling achieve the user-defined temperature versus time profile.

Figure 3:
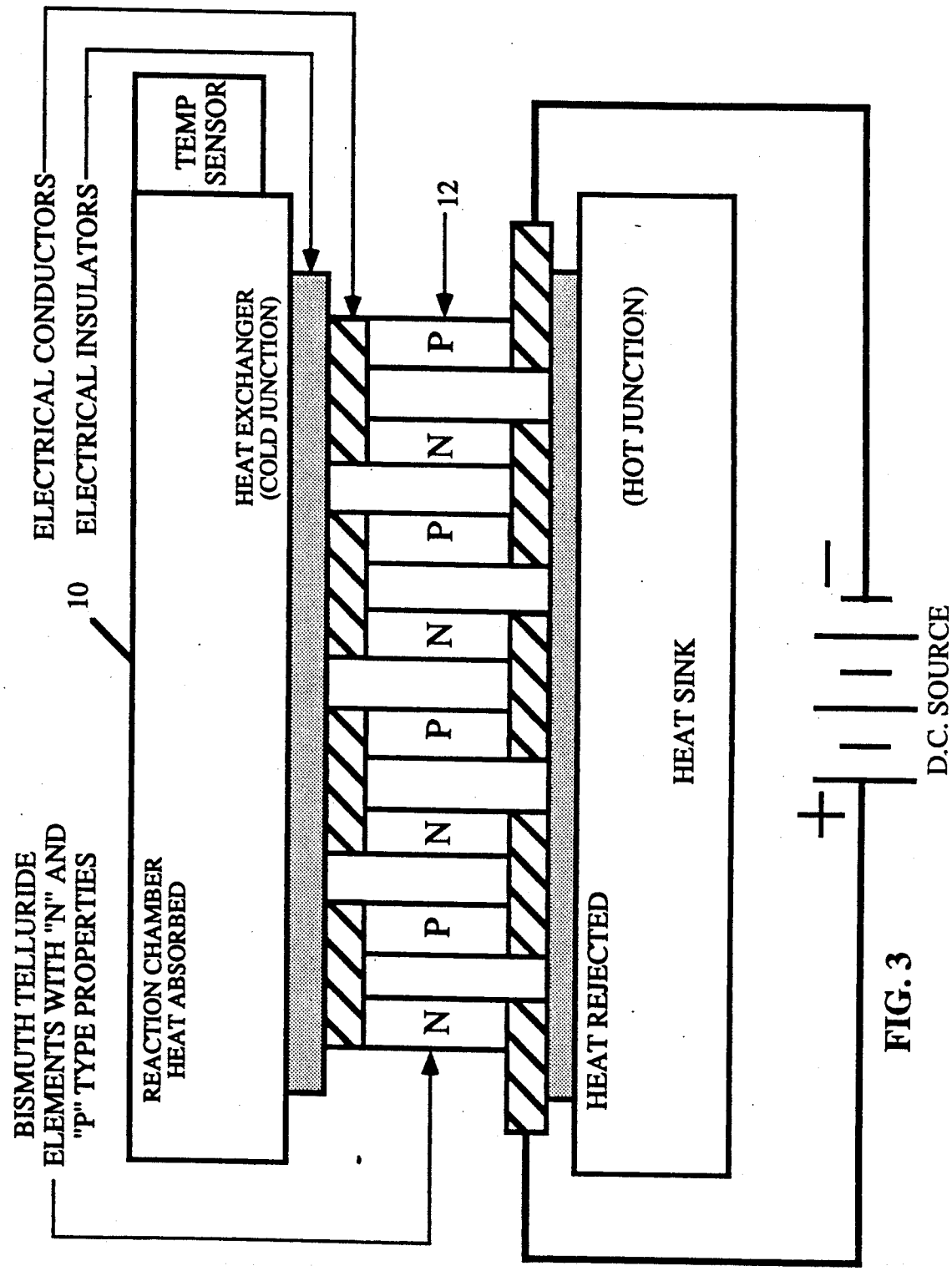
FIG. 3 is a diagram of a solid state heat pump and reaction chamber heat exchanger structure.

In a preferred embodiment, pictured in FIG. 1, one such electrically driven heating and cooling apparatus is a Peltier Frigichip® solid state thermoelectric heat pump 12, available from Melcor Corporation in Trenton, N.J. A conventional heat pump using a compressor, an evaporator and a condenser will also work for heat pump 12. Solid state heat pumps such as Peltier devices are comprised of N and P type bismuth telluride in the form of oriented polycrystalline ingots forming back to back PN junctions and with the ends soldered to copper bus bars interfaced with ceramic plates. FIG. 3 shows such an arrangement. These heat pumps heat or cool by driving currents through them in particular, known ways to move heat in either direction between a heat sink 14 and the heat exchanger 10. These solid state heat pumps have been used by Gilford Instruments Corporation to heat and cool cuvettes, and are available in wattage ranges up to and including 150 watts. These devices are capable of cooling or heating a mass of material to which they are thermal coupled to temperatures in a range from −150 to +110 degrees centigrade. Such semiconductors could be thermally coupled to the insert tubes or wells. Such semiconductors can be easily controlled to reach and maintain particular temperatures by modulating the currents which flow through them in accordance with the desired temperature level according to standard process control algorithms. The manner of designing such a solid state heat pump system is published in an application note on the FRIGICHIP series FC by Melcor (990 Spruce Street, Trenton, N.J. 08648 (609)-393-4178) which is hereby incorporated by reference.

Figure 2:
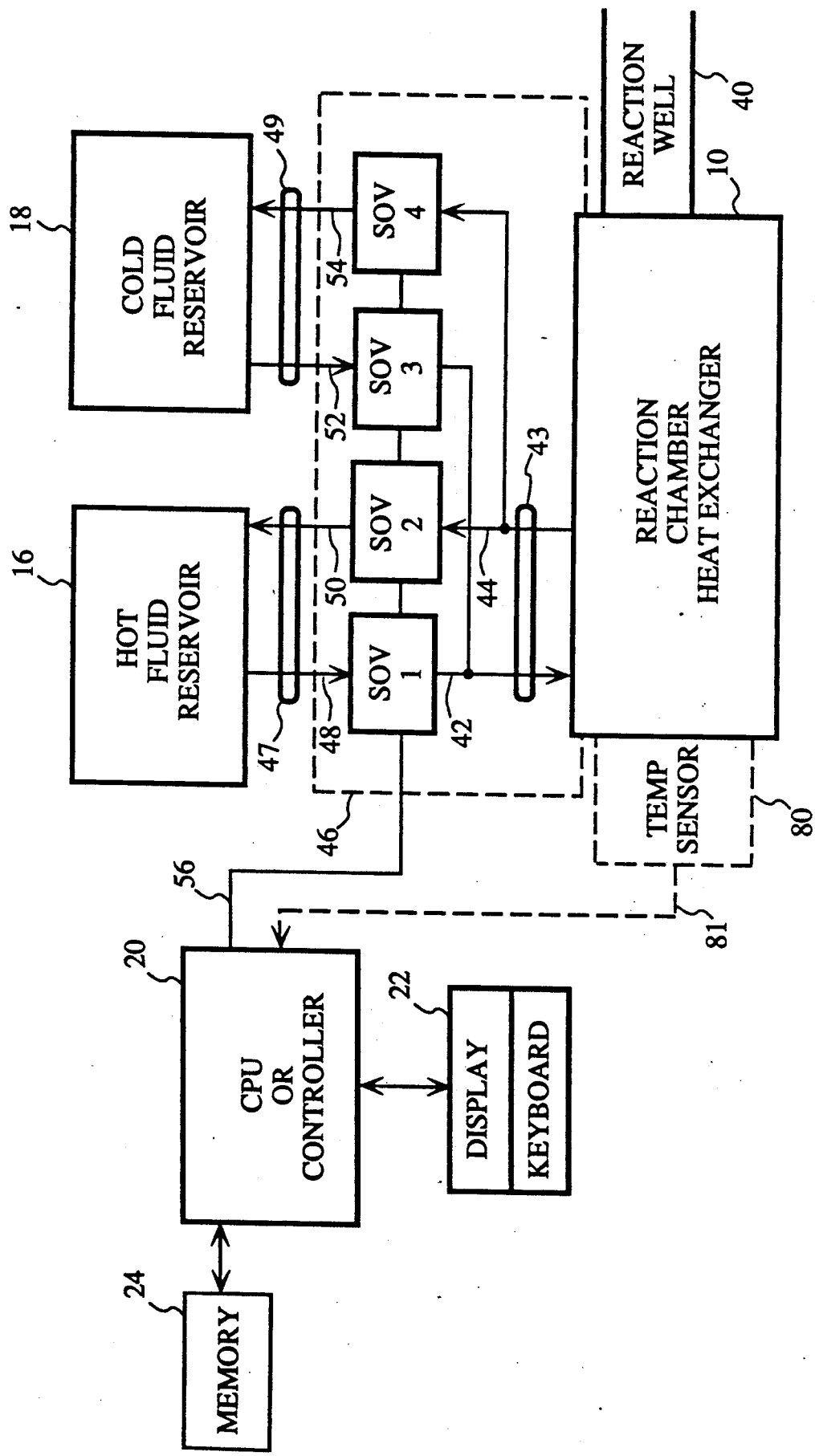
FIG. 2 is a general block diagram of a machine which can perform the thermostable enzyme amplification process herein using water baths to cycle the temperature of the reaction vessels.

In another embodiment, illustrated in FIG. 2, water baths 16 and 18 which maintain reservoirs of fluids at constant temperatures may be used. Again, heat exchanger 10 is an aluminum plate or some other metal with good heat-conducting properties. Passageways are machined or molded into the metal of the heat exchanger through which heated or cooled fluids may be pumped. In one embodiment of the machine pictured in FIG. 2, heat exchanger 10 has a fluid inlet coupled to a tube 42 and a fluid outlet coupled to a tube 44. These two tubes are coupled to the outputs of a fluid multiplexer 46. The fluid muliplexer has two pairs of input-/output ports. One pair 47 is coupled to high temperature fluid conveyance tubes 48 and 50 and the other pair 49 is coupled to low temperature fluid conveyance tubes 52 and 54. Each pair of ports has one input channel and one output channel. For example, the first pair has its input channel coupled to tube 48 and its output channel coupled to tube 50. Likewise, the output pair of the fluid multiplexer 46 has one output channel, coupled to the tube 42, and one input channel, coupled to the tube 44. The purpose of the fluid multiplexer 46 is to couple selectively either the first input pair, tubes 48 and 50, or the second input pair, tubes 52 and 54, to the output pair 43 in accordance with a select signal on a line 56. If the first pair of ports 47 is selected, the tube 48 is coupled in fluid communication to the tube 42 through an internal fluid passage in the fluid multiplexer 46 in the form of a solenoid-operated valve designated SOV 1. Likewise, the tube 50 is coupled to the tube 44 through an internal fluid channel in the fluid control muliplexer 46 in the form of a solenoid-operated valve designated SOV 2. A similar connection occurs if the second pair of ports 49 is selected.

In this manner, the temperature of the heat exchanger 10 and the fluids stored in the tubes in the reaction wells such as the well 40 may be controlled by the state of a TEMP SELECT signal on the conductor 56. In one embodiment, the fluid multiplexer 46 is implemented with four solenoid-operated valves, designated SOV's 1 through 4, which are properly interconnected with the tubes 42, 44, 48, 50, 52 and 54. However, any apparatus that can perform the fluid switching noted above will suffice. Indeed, if a solid sate or conventional heat pump 12 is used in connection with controlling the temperature of heat exchanger 10, the need for and expense of the fluid multiplexer 46 is eliminated.

The heated and cooled fluid flowing in the tubes coupled to the fluid multiplexer 46 is pumped from a high temperature fluid reservoir 16 and a low temperature fluid reservoir 18, respectively. The purpose of these reservoirs is to maintain a volume of fluid such as water or antifreeze at a constant temperature. Generally, the high temperature fluid is maintained at a constant temperature of 80° to 105° C., preferably 90°-100° C., and the low temperature fluid is maintained at a constant temperature of about 35°-60° C., preferably about 37° to 50° C. The reservoirs 16 and 18 are adjustable in terms of the temperatures at which they maintain their fluid reservoirs. Water bath 18 is preferably adjustable so as to be able to achieve a reservoir temperature anywhere in the range from −35° to +150° C. The water bath 18 preferably has a water capacity of 13 liters and a rapid chill-down feature so as to have a cool-down rate in excess of 100° C. per minute. This helps minimize temperature stabilization time. Any type of fluid heating and cooling apparatus which can achieve and maintain such temperatures over the duration of the amplification process will suffice for purposes of the invention. In the preferred embodiment, VWR 1135 and VWR 1155 water baths are used.

The enzyme used in the amplification process is added to the other reagents in the reaction well 40 initially.

The enzyme employed herein is a thermostable enzyme, as defined hereinbelow, which can withstand the high temperatures employed to denature the nucleic acid strands. Therefore, a liquid handler is not necessary to add the thermostable enzyme to the reaction well at certain points in the temperature profile. The enzyme may stay in the reaction well 40 at all times.

Figure 5:
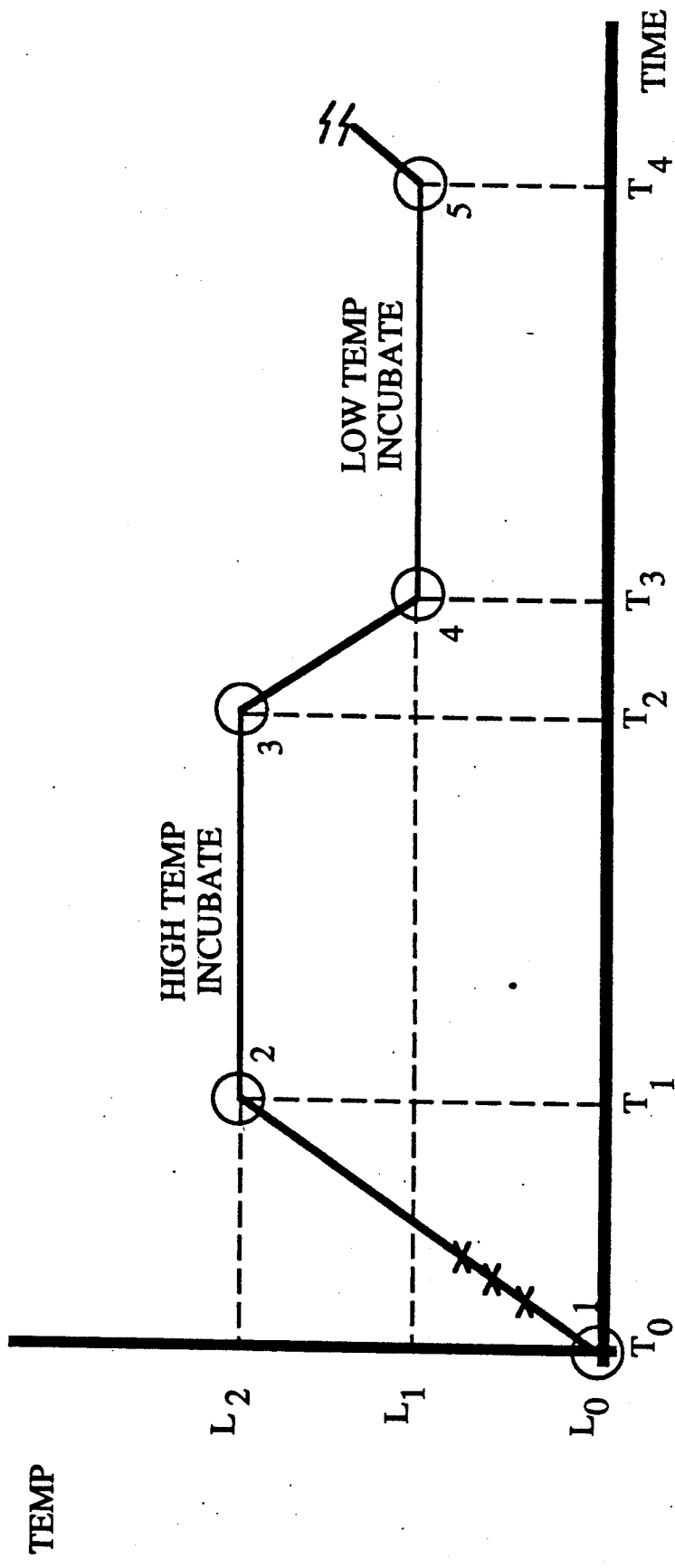
FIG. 5 is a diagram of a typical user-defined temperature profile.

Control over the temperature of the reaction vessel is maintained by the CPU 20 in the case of either the embodiment of FIG. 1 or the embodiment of FIG. 2. The CPU runs a control program which will be describe in moᵢe detail below. Basically, the control program, which is stored in a memory 24, controls the heat pump 12 or the fluid multiplexer 46. The user is interrogated by the control program thought the CPU 20 and a display/keyboard user interface 22 regarding what temperature profile the user wishes to run. The user responds with temperatures on the desired profile and the times the user wants those temperatures to be achieved. These responses are read by the CPU 20 from a user interface 22. The queries to the user are displayed on the display of the user interface 22, and the user's responses are received via the keyboard thereof. User responses in the form of time and temperature checkpoints on the desired profile are stored in a RAM 24. A typical time versus temperature profile is shown in FIG. 5. The CPU then generates the proper control signals to cause heat to be added to or taken away from heat exchanger 10 to maintain the reaction vessel 40 on the desired temperature profile.

In the case of the embodiment shown in FIG. 1, the control signals generated by the CPU 20 to control the heat pump consist of a pulse train of pulse width modulated control pulses. These pulses are coupled to a heat pump interface circuit 26 on a line 56.

Figure 4:
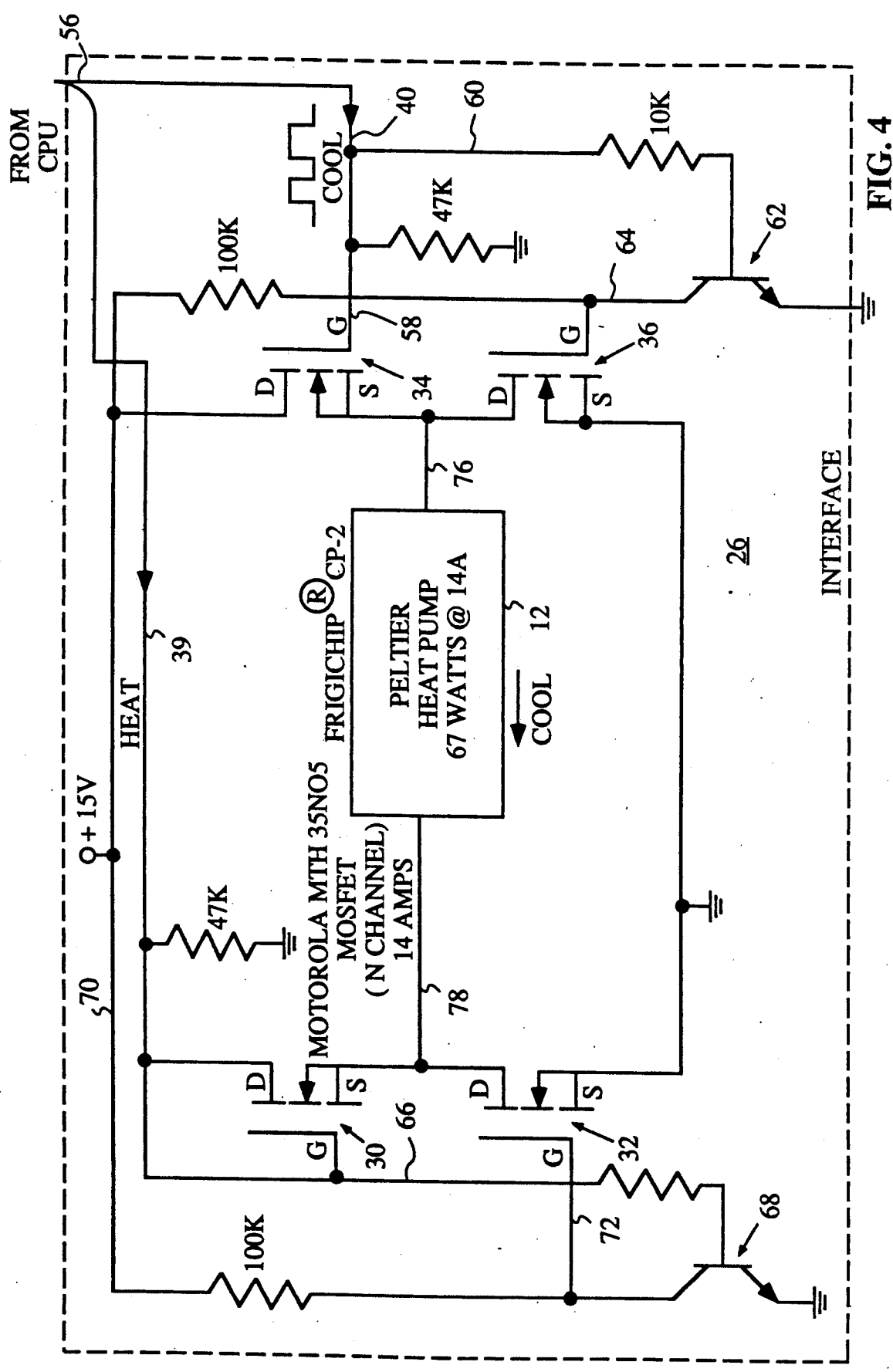
FIG. 4 is a schematic diagram of the interface unit for a solid state heat pump.

The circuitry of the heat pump interface is shown in more detail in FIG. 4. The purpose of this interface circuit is to convert the pulse width modulated control pulses at logic levels from the CPU into high current pulses of the same duration through the solid state heat pump 12. Four N channel MOSFET power transistors 30, 32, 34 and 36 are used for this purpose. These transistors are connected in a bridge arrangement with the solid state heat pump 12 as a load. This bridge reverses the direction of current flow through the load 12 under the influence of two control signals from the CPU on lines 39 and 40. When the cool control signal on line 40 is active, the transistors 34 and 32 are turned on and the transistors 30 and 36 are turned off. The reason for this is that the cool signal is coupled to the gate of the transistor 34 by the line 58 and turns this transistor on. The cool signal also turns on a transistor 62 which pulls the gate voltage on the line 64 down to ground potential thereby turning off transistor 36.

The heat control signal on line 39 is always in the opposite binary state as the cool control signal on line 40. When cool is active, the gate 66 of transistor 30 is low at logic 0 and this transistor will be off. The logic 0 on line 66 also turns off a transistor 68, which allows the +15 volt voltage on line 70 to drive the gate 72 of the transistor 32 to a logic 1 level. This turns on transistor 32, thereby completing a current path from right to left through the load 12, i.e., from line 70 and the power supply through the drain and source of transistor 34, through line 76, the load 12 and line 78, and through the drain and source of transistor 32 to ground.

The reverse situation occurs when the heat signal is active. In this case, transistors, 30, 68 and 36 are on and transistors 34, 62 and 32 are off.

In the embodiment shown in FIG. 2, the interface circuit of FIG. 4 is not necessary. However, some solenoid drive interface will be necessary to allow the CPU to control the solenoid-operated valves. The design of a suitable interface will be well known to those skilled in the art.

The CPU 20 in the embodiments of either FIG. 1 or FIG. 2 may be any one of a number of different types of computers. It may be a custom designated computer, an off the shelf controller such as the Model 2010 PuP ™ controller available from LFE Corporation in Clinton, Mass., or it may be an IBM or other personal computer, minicomputer or mainframe. Whatever type of computer is used, it must be capable of accepting data from the user regarding the desired temperature profile either in real time or at the time the computer is installed. There should be some mechanism to calculate a "set point" in embodiments using actual temperature sensors such as the sensors 80 in FIGS. 1 and 2. A "set point" is a target temperature taken from the user-defined temperature profile which can be used in calculating an error signal based upon the error between the actual temperature and the target temperature. Refer now to typical temperature profile illustrated in FIG. 5. Typical user-defined temperature profile checkpoints are shown as small circles. Checkpoint 1 is characterized by a temperature level $L_0$ at the reaction vessel 40 at time $T_0$. Checkpoint 2 is characterized by a temperature level $L_2$ at a later time $T_1$. Checkpoint 3 is characterized by the existence of a temperature level $L_2$ at the reaction vessel 40 at a time $T_2$ and so on. The sections between checkpoints will be called "legs".

The CPU 20, in embodiments that do not use actual temperature sensors, must be programmed to keep tack of the time during which heating or cooling action takes place. Further, the CPU must be capable of storing one or more empirically determined times against which actual elapsed time during a heating or cooling leg may be compared. These empirically determined times are experimentally determined by the user. Typically the user will set a certain current flow during the design of the solid state heat pump interface of FIG. 4, and this current flow will be used for all heating and cooling in the embodiment of FIG. 1. In the case of the embodiment of FIG. 2, the user must set the temperature level of the hot and cold reservoirs 16 and 18. The fixed current in the case of the embodiment of FIG. 1 and the fixed temperature level for the reservoirs in the case of the embodiment of FIG. 2 will establish a user-defined heating or cooling rate of change for a given mass of the heat exchanger 10 and reaction vessel and contents. The user will then define the desired checkpoints and determine the times it takes to heat or cool to these checkpoints at the fixed heating or cooling rate. If the times taken to reach the checkpoints are not acceptable, the heating or cooling rate must be adjusted until the times are right. Of course, this approach is not very flexible if the heating or cooling rate cannot be adjusted in real time, since the slope of the heating and cooling legs must always be the same using these embodiments, which will be referred to as the "empirical" class of embodiments.

An alternative empirical type embodiment class is to program the CPU 20 to use different heating and cooling rates on each leg. This allows each leg to have a different slope. This may be accomplished using pulse width modulation, but not using any temperature sensor and actual temperature feedback (illustration of the temperature sensors in dashed lines is intended to symbolize these embodiments) in either of the embodiments of FIGS. 1 and 2. In these alternative embodiments, the heating or cooling current flow (or fluid flow in the case of the embodiment of FIG. 2) is a stream of pulses. The duty cycle is controlled by the CPU 20 such that if a greater heating or cooling rate is needed, the "on" time of the pulses is increased. The reverse situation applies if the heating or cooling rate is to be decreased. In these embodiments, the user has more freedom to adjust the temperature profile because the empirical time and heating and cooling rate may both be adjusted until the interval between and temperature levels at the checkpoints are as desired.

Generally, this requires more work on the part of the user than the preferred embodiment and is not as accurate. The reason is that once the user establishes a fixed heating or cooling rate for each leg, that rate is fixed for that leg and cannot be altered in real time to account for changing conditions. That is, in these embodiments, the CPU 20 does not alter the heating and cooling rates in real time to correct for changing ambient conditions or other variations.

The preferred embodiment uses actual temperature feedback and a closed loop control system to control the heating and cooling rate. This allows real time error signal generation to conform the actual temperature profile to the desired temperature profile. To implement the preferred embodiment, the CPU 20 is programmed to prompt the user to enter "checkpoints" for the desired temperature profile. Then, the CPU 20 starts a clock running to measure elapsed time and periodically calculates "set points" based upon the desired temperature profile defined by the checkpoints. The calculated set points are targets to achieve and are used in another software routine to generate an error signal.

The error signal generation routine reads the actual temperature of the reaction chamber from the temperature sensor 80 and compares it to the desired temperature defined by the set point. Typical set points calculated for the temperature profile of FIG. 5 are shown by the three x's on leg 1 between checkpoints 1 and 2. The comparison yields an error signal which is used by a pulse width modulation routine to generate the control signals which cause heating or cooling of the reaction chamber by the heating and cooling apparatus.

The pulse width modulation routine calculates the necessary "on" time or duty cycle for the heat and cool control signals and determines which of these two control signals should be active. The proper control signals are then generated and written to the solid state heat pump interface 26 or to the fluid multiplexer or other heating and cooling apparatus.

Figure 6A:
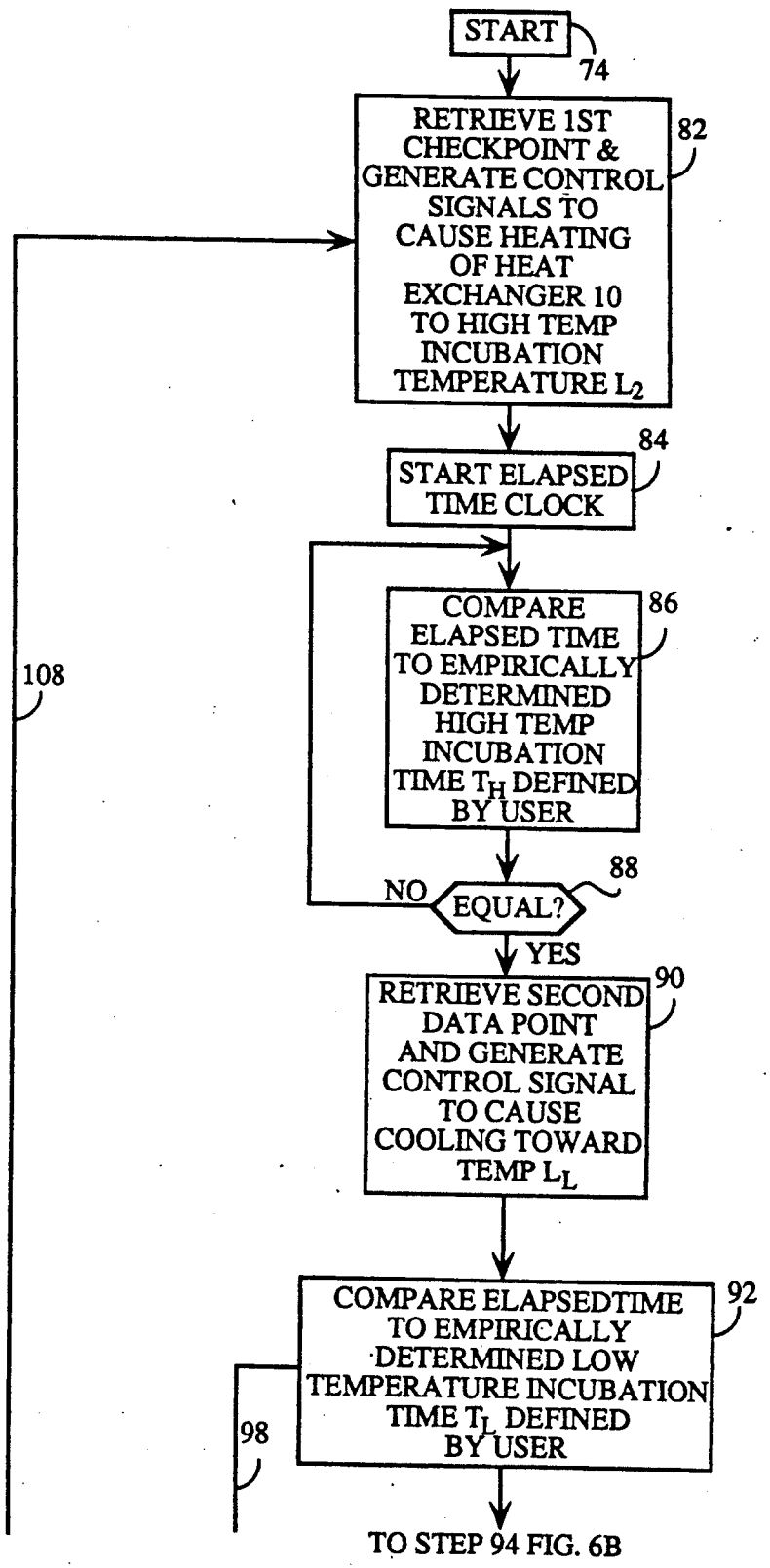
FIG. 6 is comprised of two halves labeled FIG. 6A and FIG. 6B and comprises a flow diagram for the control software for the empirical embodiments which do not use feedback of the actual reaction chamber temperature.
Figure 6B:
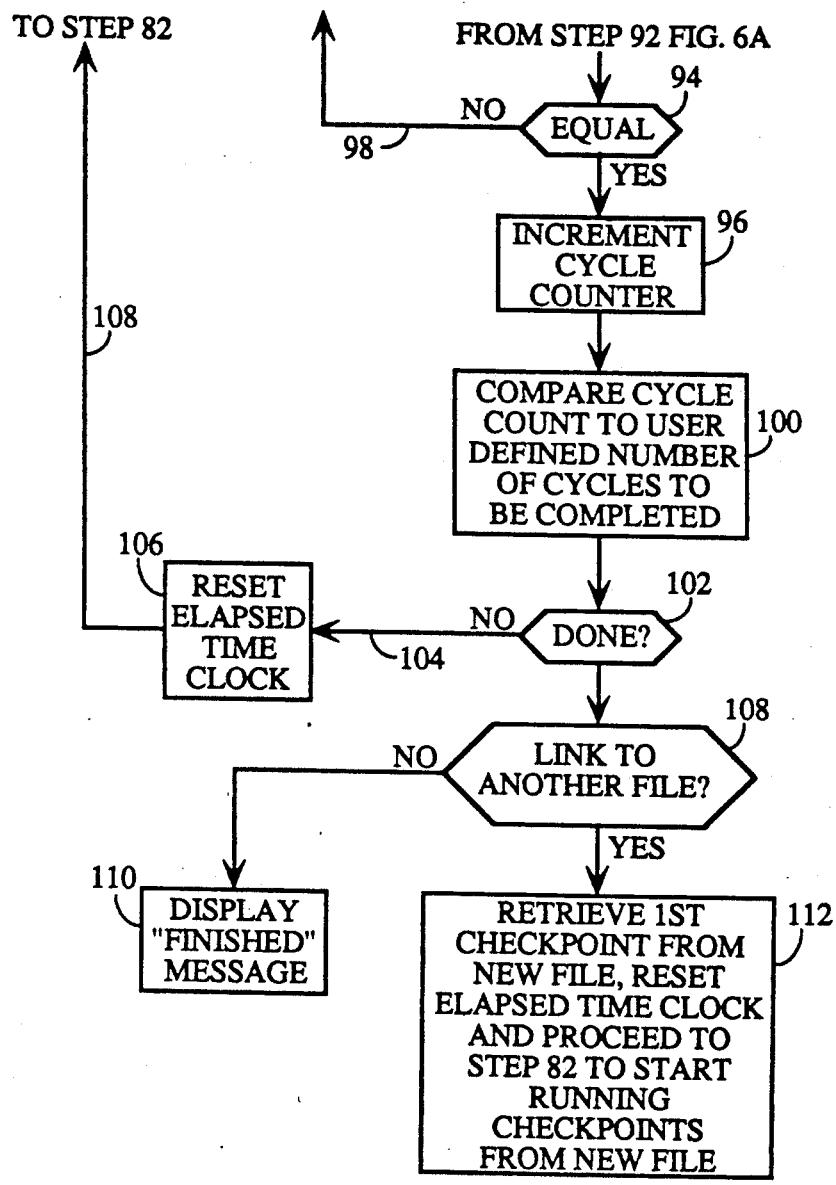

The amplification process which the machine must perform for an empirical time embodiment not using a sensor 80 for the embodiments shown in FIGS. 1 and 2 is given in flow chart format in FIG. 6. The process starts at block 74 with a command from the user to start the amplification processing. Prior to this time the user must have loaded the proper enzyme into the reaction chambers 40 in heat exchanger 10 along with the nucleic acid sequence(s) to be amplified plus the proper reagents defined below. In some embodiments, the reaction chambers 70 in the heat exchanger 10 may be loaded with the proper starting materials automatically by a conventional liquid handler (not shown) such as a Pro/Pette ® liquid handler from Cetus Corporation in Emeryville, Calif.

Upon receiving the start command, the CPU 70, in a step 82, retrieves the first checkpoint data and issues the proper signal on the temperature select line 56 in FIG. 2 (the method of operation of FIG. 6 is equally applicable to the embodiment shown in FIG. 1) to cause the opening of the SOV pair 46 to heat the heat exchanger 10 to a high temperature equal to a user-defined level, which will be hereafter referred to as temperature variable $L_H$. In some embodiments, temperature variable $L_H$ will not be a variable, but will be a constant fixed at the temperature of the high temperature reservoir 16. In other non-empirical embodiments using actual temperature feedback data, the variable $L_H$ will be user-defined and the CPU 70 will monitor the temperature of the reaction chamber 40 and issue the proper command signal to the temperature control apparatus (solenoid-operated valves plus reservoirs or heat pump interface plus heat pump) to cause it to heat the heat exchanger 10 until the desired temperature is reached, and then will issue the proper commands to the temperature control apparatus to cause the desired temperature to be maintained. No monitoring of the temperature of heat exchanger 10 is done by the CPU 20 in the empirical embodiment currently under discussion. However, in the preferred embodiment, the temperature of the heat exchanger 10 and reaction vessel is monitored by the CPU 40, and an error signal is generated by comparison of the actual temperature to the calculated set points from the user-defined checkpoints to control the temperature of the heat exchanger 10 according to a user-defined time versus temperature profile.

The temperature of the reaction chamber 40 during this high-temperature incubation should be maintained at 80°–105° C., preferably 90°–100° C. The minimum temperature at which the denaturation process will occur is 80° C. The temperature rise profile to the temperature $L_H$ should be as rapid as possible, generally 0.5 to 5 minutes, more preferably 1–3 minutes, to save time in the overall completion time of one cycle.

Of course, before all this may happen, the user must enter the checkpoint data. The steps to prompt the user for the checkpoints, to store the data so entered, and to retrieve it sequentially for calculation of set points are conventional and are not critical to the process, so they are not shown.

The amplification process of these empirical time embodiments involves a high-temperature incubation period for a user-defined, empirically determined time from start of heating to end of incubation. For implementation of the incubation, the computer starts a clock in step 84 and times the elapsed time from the start of heating toward temperature level $L_H$ and compares the elapsed time to a high-temperature incubation time, $T_H$, entered by the user as symbolized by step 86. In the preferred embodiments, the incubation time variable may be set at any desired non-empirical value by the user in real time.

In other embodiments, the time $T_H$ (heating and high temperature incubation time) may be a fixed time which is experimentally determined and then "burned" into a ROM for permanent storage. In some embodiments, the CPU 20 may monitor the temperature of the heat exchanger 10 such as by use of the temperature sensor 80 shown attached to heat exchanger 10 in FIG. 1 and coupled to the CPU 20 through a line 81, and begin timing the high temperature incubation period when plate 1 reaches the temperature of temperature variable $L_H$.

In the embodiment of FIG. 6, the user sets variable $T_H$ at a time which is empirically established to include the time it takes plate 1 to reach the desired temperature $L_H$ plus the desired time for high-temperature incubation at temperature $L_H$. In embodiments where the computer starts tracking elapsed time only when the desired temperature $L_H$ is reached, i.e., where a temperature sensor 80 is used, the variable $T_H$ may be set by the user at the amount of time desired for high-temperature incubation at temperature $L_H$ without regard for the amount of time it takes for plate 1 to reach temperature $L_H$. In the preferred embodiment, temperature $L_H$ is fixed at 90°–100° C.

When the elapsed time at temperature $L_H$ equals the desired incubation time as determined by step 88, the CPU 20 sends the proper command to the heating and cooling apparatus to cause plate 1 to be cooled toward a low temperature incubation temperature $L_L$ set by the user. This is symbolized by step 90. Step 90 represents the transmission by the CPU 20 of a command, in the case of the embodiments of FIG. 2, to the fluid control multiplexer 46 to select the tubes 52 and 54 to couple to the tubes 42 and 44 such that fluid at the temperature of low-temperature fluid reservoir 18, set at $L_L$ by the user manually, begins to flow through the heat exchanger 10. In other embodiments, the CPU 20 may simply send a command to the heating and cooling apparatus to turn on an electrically driven refrigeration unit thermally coupled to plate 1, such as the Peltier heat pump 12. The range of chill-down rates from the high temperature to the low temperature which may be successfully used is governed by a balance of considerations. A very rapid chill-down, such as by using dry ice to bring the temperature of the reaction chamber down immediately, will inhibit or stop the amplification process. On the other hand, slow chill-down will lengthen the overall completion time of one cycle. Preferably, the chill-down rate will range from about 0.5 to 5 minutes, preferably in the range from 1 to 3 minutes. In the preferred embodiment, a fixed temperature within the range of from about 35° to 60° C. is set by the user by manual adjustment of low-temperature fluid reservoir 18 to maintain this temperature in the case of the embodiment of FIG. 2. In the case of the embodiment of FIG. 1, the CPU 20 will establish the proper direction of current flow and duty cycle based upon the user entered data for $L_L$. The duty cycle may be based upon user-defined data for the particular leg or may be fixed in either type embodiment. The temperature range of from about 35° to 60° C. is the optimum temperature for the thermostable enzyme used in the amplification protocol. The broad range of temperatures at which the amplification protocol can be successfully performed is about 30°-35° to 105° C.

The next step is symbolized by step 92 and represents the process of measuring the elapsed time and comparing it to the user-defined low temperature incubation time $T_L$. The optimum time it takes to reach temperature $L_L$ is not exactly known, but approximately 1-3 minutes is known to be effective. In the empirical embodiments, the CPU 20 does not monitor the temperature of plate 1; it only keeps track of the elapsed time since the command was issued to chill plate 1. The user must empirically determine how long it takes to reduced the temperature of plate 1 to temperature $L_L$. The CPU 20 in step 92 constantly compares the actual elapsed time to the user-defined time $T_L$. When the required time has passed, processing proceeds to stop 94.

Step 94 symbolizes the process of monitoring for completion of the low-temperature incubation. In some embodiments, the computer CPU 20 begins tracking elapsed time when temperature $L_L$ is reached. Step 94 represents the process of the computer comparing the actual elapsed time to a low-temperature incubation time, user-defined variable $T_L$. In some embodiments, this variable is a real time, user-defined time stored in the memory of the computer, while in other embodiments, the time $T_L$ is fixed and permanently stored after being empirically determined.

As soon as the elapsed time equals the desired low-temperature incubation time $T_L$, step 94 causes processing to proceed to a step 96, which increments a software cycle counter to mark the end of the first cycle. If the actual elapsed time does not equal the time $T_L$, processing proceeds on line 98 to step 92 for another comparison of elapsed time to desired time $T_L$. After step 96, the CPU 20 proceeds to step 100.

Step 100 and step 102 represent the process of comparison of the cycle count to a user-defined variable in memory representing the desired number of cycles. In some embodiments, the desired number of cycles is a fixed number, but in the preferred embodiment, the desired number of cycles is a user-defined number. This gives the user the flexibility to vary the number of cycles of amplification performed to account for the differing efficiencies of amplification of different nucleic acid sequences, as described further below. If the cycle count does not match the desired number of cycles, processing proceeds via line 104 to step 106 to reset the elapsed time clock, and from there processing proceeds to step 82 via line 108 where another cycle is begun. If the desired number of cycles has been performed, then processing proceeds to step 108. There it is determined whether the user desires to run another temperature profile stored in another "file" or database. Every temperature profile entered by the user has a link data field in which there is stored the file identification of the next file or temperature profile to be run, if any. The contents of this link field are read in step 108. If the user has made no entry to the link field, then processing process to step 110, and a finished message is displayed. If step 108 finds a file number in the link field, then processing proceeds to step 112. This step resets the elapsed time clock, and retrieves the first checkpoint from the new file. Processing then proceeds, starting at step 82, to run the temperature profile determined by the checkpoints in the new file.

The control process of FIG. 6 shows only two checkpoints for the temperature profile. In other embodiments, a greater number of checkpoints may be used so long as there is a generally high temperature incubation and a generally low temperature incubation at the proper temperatures for sufficient times.

Figure 7A:
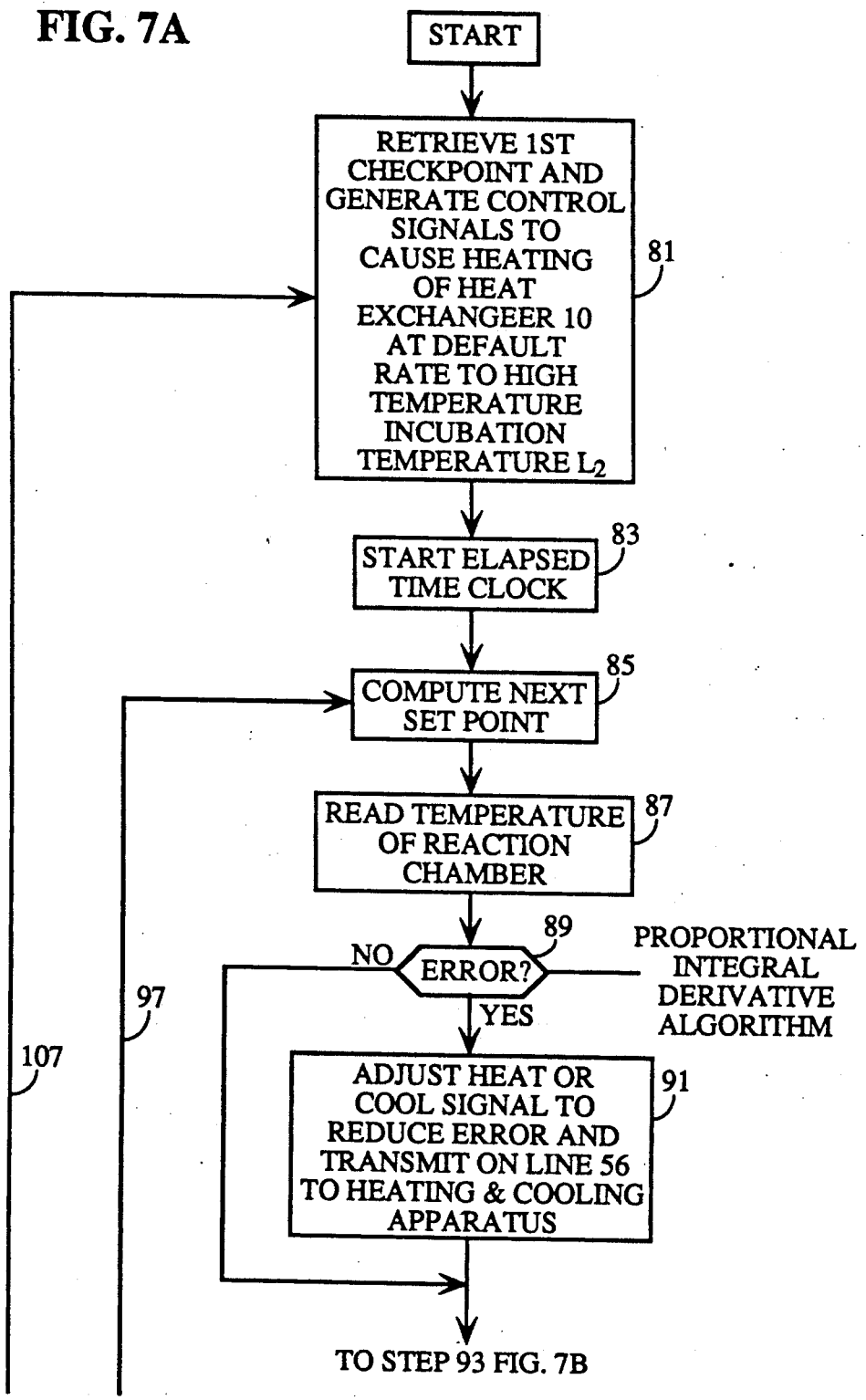
FIG. 7 is comprised of two halves labeled FIG. 7A and FIG. 7B and comprises a flow diagram for the control software for the preferred embodiments which use actual temperature feedback signals to monitor the actual temperature of the reaction chamber and compare it to the desired temperature profile.

In the preferred non-empirical "closed loop" embodiments running the process shown in FIG. 7, the CPU 20 in step 81 starts the heating for log 1 for the user-defined temperature profile at a default rate and starts the clock in step 83. The CPU 20 then computes a set point in step 85 as a target temperature and continuously monitors the temperature of plate 1 in step 87 and compares it to the set point on the user-defined temperature profile. Step 85 periodically updates the set point by computing the slope of the temperature profile between user-defined checkpoints and calculating the new set point based upon the slope and elapsed time at the time of the calculation. An error signal based on the comparison can be generated by the CPU 20 in step 89. This error signal is then converted to the proper control signal to control the heating and cooling apparatus in step 91. In the case of a solid state heat pump, the error signal is used to change the duty cycle. The updated control signal is then output on the line 56 to cause the heating and cooling apparatus to adjust the reaction chamber temperature. If plate 1 became hotter than the desired profile for a particular set point, then the cold fluid would be switched on to cool it in the embodiment of FIG. 2. In the case of the embodiment of FIG. 1, the direction of current flow through the solid state heat pump could be reduced or the "on" time of the heat pulse duty cycle could be reduced to reduce the error signal magnitude toward zero.

In the preferred embodiment control process of FIG. 7, the CPU 20 begins timing the elapsed time at the same time the command is sent to the temperature control apparatus to begin heating plate 1 to the high temperature incubation level in step 81. After step 91 (or step 89 if no error is present) is performed in FIG. 7, step 93 is performed to compare the actual elapsed time to the user-defined time stored in memory at which the next checkpoint shall have been reached. If the elapsed time is equal to or greater than the checkpoint time, processing proceeds to step 95 to retrieve the time and temperature data for the next checkpoint.

If the elapsed time is less than the time to the next checkpoint, processing returns on line 97 to step 87 on FIG. 7. The next set point is then calculated, and processing continues as described above.

The error signal computation of step 89 is done using any known proportional control algorithm. Such algorithms are well known and are described in Shinskey, *Process Control Systems*, 2d ed., Chapter 1 (McGraw Hill 1979) ISBN 0-07-056891x, which is hereby incorporated by reference.

After retrieval of the time and temperature data for the next checkpoint, the CPU determines in step 99 whether the complete temperature profile has been processed. If the cycle has not been completed, processing returns on line 97 to step 87 to compute the next set point. Processing then continues from step 87 as defined above.

If the temperature profile has been completed, then step 101 is performed to increment the cycle counter (a software counter) to indicate than one complete cycle through the temperature profile has been completed. Next, the CPU 20 retrieves from memory the value from a data field in the database indicating the desired number of cycles through the particular temperature profile just completed. This is symbolized by step 103. This value is retrieved from a database that is filled with the checkpoint data and other information supplied by the user via the user interface 22 in FIGS. 1 and 2 and stored in RAM 24. In step 105, the number of cycles completed is compared to the user-defined desired number of cycles.

If the desired number of cycles have not been completed, then processing returns to step 81 on line 107. The first checkpoint in the same profile is then retrieved, and the processing of the same checkpoints in the current temperature profile starts over again as described above.

If step 15 indicates that the desired number of cycles through the temperature profile have been completed, then step 109 is performed to determine file linkage. Some users may wish to run one temperature profile for some number of cycles, x, and then run a different temperature profile for a different number of cycles, y, and so on for several different temperature profiles. Each temperature profile database is given a file identification number, and each file has a link field in the database for that profile. The content of this link field is retrieved in step 109 and is the file number of the next temperature profile to be performed, i.e., the next file to be "run". If the contents of this link field are zero or some other predetermined code, then no linking is to occur and processing stops with an indication on the display that such is the case. If there is a linkage, step 111 is performed to retrieve the first checkpoint of the new profile and processing continues from step 81 as described above. The linking process is repeated at the end of the next temperature profile and the next until no linking address is found. Processing is then complete.

Amplification Protocol

The amplification protocol automated by the present invention is a process for amplifying existing nucleic acid sequences using thermostable enzymes. The amplification process is disclosed and claimed in copending U.S. patent application Ser. No. (Cetus Case 2177.3) filed concurrently herewith, wherein Cetus Corporation is the assignee, as in the present invention, entitled "Process for Amplifying, Detecting, and/or Cloning Nucleic Acid Sequences Using A Thermostable Enzyme." The disclosure for said application is herein incorporated by reference.

More specifically, the amplification method involves amplifying at least one specific nucleic acid sequence contained in a nucleic acid or a mixture of nucleic acids, wherein if the nucleic acid is double-stranded, it consists of two separated complementary strands of equal or unequal length, which process comprises:

(a) contacting each nucleic acid strand with four different nucleotide triphosphates and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said contacting being at a temperature which promotes hybridization of each primer to its complementary nucleic acid strand;

(b) contacting each nucleic acid strand, at the same time as or after step (a), with a thermostable enzyme which catalyzes combination of the nucleotide triphosphates to form primer extension products complementary to each strand of each nucleic acid;

(c) heating the mixture from step (b) for an effective time and at an effective temperature to promote the activity of the enzyme, and to synthesize, for each different sequence being amplified, an extension product of each primer which is complementary to each nucleic acid strand template, but not so high as to separate each extension product from its complementary strand template;

(d) heating the mixture from step (c) for an effective time and at an effective temperature to separate the primer extension products from the templates on which they were synthesized to produce single-stranded molecules, but not so high as to denature irreversibly the enzyme;

(e) cooling the mixture from step (d) for an effective time and to an effective temperature to promote hybridization of each primer to each of the single-stranded molecules produced in step (d); and (f) heating the mixture from step (e) for an effective time and to an effective temperature to promote the activity of the enzyme and to synthesize, for each different sequence being amplified, an extension product of each primer which is complementary to each nucleic acid strand template produced in step (d), but not so high as to separate each extension product from its complementary strand template, wherein steps (e) and (f) may be carried out simultaneously or sequentially.

Steps (d)-(f) may be repeated until the desired level of sequence amplification is obtained.

The amplification method is useful not only for producing large amounts of an existing completely specified nucleic acid sequence, but also for producing nucleic acid sequences which are known to exist but are not completely specified. In either case an initial copy of the sequence to be amplified must be available, although it need not be pure or a discrete molecule.

The term "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleotide triphosphates and a thermostable enzyme at a suitable temperature and pH.

The primer is preferably single-stranded for maximum efficiently in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 or more nucleotides, although it may contain more for fewer nucleotides. Short primer molecules generally require cooler temperatures to form sufficiently stable hybrid complexes with template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

As used herein, the terms "restriction endonucleases" and "restriction enzymes" refer to bacterial enzymes each of which cut double-stranded DNA at or near a specific nucleotide sequence.

As used herein, the term "thermostable enzyme" refers to an enzyme which is stable to heat and is heat resistant and catalyzes (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis teminrates, producing molecules of different lengths. There may be thermostable enzymes, however, which initiate synthesis at the 5' end and proceed in the other direction, using the same process as described above.

The thermostable enzyme herein must satisfy a single criterion to be effective for the amplification reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° to about 105° C. for a time depending mainly on the temperature and the nucleic acid length, typically about 0.5 to four minutes. Higher temperature may be tolerated as the buffer salt concentration and/or GC composition of the nucleic acid is increased. Preferably, the enzyme will not become irreversibly denatured at about 90°-100° C.

The thermostable enzyme herein preferably has an optimum temperature at which it functions which is higher than about 40° C., which is the temperature below which hybridization of primer to template is promoted. The higher the temperature optimum for the enzyme, the grater the specificity and/or selectivity of the primer-directed extension process. However, enzymes which are active below 40° C., e.g., at 37° C., are also within the scope of this invention provided they are heat-stable. Preferably, the optimum temperature ranges from about 50° to 80° C., more preferably 60°-80° C.

Examples of enzymes which have been reported in the literature as being resistant to heat include heat-stable polymerases, such as, e.g., polymerases extracted from the thermophilic bacteria *Thermus flavus, Thermus ruber, Thermus thermophilus, Bacillus stearothermophilus* (which has a somewhat lower temperature optimum than the others listed, *Thermus aquaticus, Thermus lacteus, Thermus rubens,* and *Methanothermus fervidus.*

The preferred thermostable enzyme herein is a DNA polymerase isolated from *Thermus aquaticus,* strain YT-1, and purified as described in copending U.S. application Ser. No. filed concurrently herewith Cetus Docket 2303, entitled "purified Thermostable Enzyme," the disclosure of which is incorporated herein by reference, Briefly, *Thermus aquaticus* cells are grown and the polymerase is isolated and purified from the crude extract using the first five steps indicated by Kaledin et al., *Biokhimiya,* 45, 644-651 (1980), the disclosure of which is incorporated herein by reference. During the fifth step (DEAE column at pH 7.5), an assay is made for contaminating deoxyribonucleases (endonucleases and exonucleases) and only those fractions with polymerase activity and minimal nuclease contamination are pooled. The last chromatographic purification step uses a phosphocellulose column suggested by Chien et al., J. *Bacteriol.,* 127:1550-1557 (1976), the disclosure of which is incorporated herein by reference. Nuclease(s) and polymerase activities are assayed, and only those polymerase fractions with minimal nuclease contamination are pooled.

While Kaledin et al. And Chien et al. report a purified enzyme with a molecular weight of 62-63 kdaltons, data using the purified protocol described above suggest a molecular weight of about 86-90 kdaltons.

In general, the amplification process involves a chain reaction for producing, in exponential quantities relative to the number of reaction steps involved, at least one specific nucleic acid sequence given (a) that the ends of the required sequence are known in sufficient detail that oligonucleotides can be synthesized which will hybridize to them, and (b) that a small amount of the sequence is available to initiate the chain reaction. The product of the chain reaction will be a discrete nucleic acid duplex with termini corresponding to the ends of the specific primers employer.

Any nucleic acid sequence, in purified or nonpurified form, can be utilized as the staring nucleic acid(s), provided it contains or is suspected to contain the specific nucleic acid sequence desired. Thus, the process may employ, for example, DNA or RNA, including messenger RNA, which DNA or RNA may be single-stranded or double-stranded. In addition, a DNA-RNA hybrid which contains one strand of each may be utilized. A mixture of any other nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the $\beta$-globin gene contained in whole human DNA (as exemplified in the Saiki et al. article, supra) or a portion of a nucleic acid sequence due to a particular microorganism which organism might constitute only a very minor fraction of a particular biological sample. The starting nucleic acid sequence may contain more than one desired specific nucleic acid sequence which may be the same or different. Therefore, the amplification process is useful not only for producing large amounts of one specific nucleic acid sequence, but also for amplifying simultaneously more than one different specific nucleic acid sequence located on the same or different nucleic acid molecules.

The nucleic acid(s) may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi, or amniotic cells by a variety of techniques such as that described by Maniatis et al., *Molecular Cloning* (1982), 280-281.

If probes are used which are specific to a sequence being amplified and thereafter detected, the cells may be directly used without extraction of the nucleic acid if they are suspended in hypotonic buffer and heated to about 90°100° C., until cell lysis and dispersion of intracellular components occur, generally 1 to 15 minutes. After the heating step the amplification reagents may be added directly to the lysed cells.

Any specific nucleic acid sequence can be produced by the amplification process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid sequence of defined length. The greater the knowledge about the bases at both ends of the sequence, the greater can be the specificity of the primers for the target nucleic acid sequence, and thus the greater the efficiency of the process.

It will be understood that the world "primer" as used hereinafter may refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be homologous with the end of the desired sequence to be amplified.

The oligonucleotide primers may be prepared using any suitable method, such as, for example, the phosphotriester and phosphodiester methods described above, or automated embodiments thereof. In one such automated embodiment, diethylphosphoramidites are used as starting materials and may be synthesized as described by Beaucage et al., *Tetrahedron Letters* (1981), 22:1859-1862. One method for synthesizing oligonucleotides on a modified solid support is described in U.S. Pat. No. 4,458,066. It is also possible to use a primer which has been isolated from a biological source (such as a restriction endonuclease digest).

The specific nucleic acid sequence is produced by using the nucleic acid containing that sequence as a template. The first step involves contacting each nucleic acid strand with four different nucleotide triphosphates and one oligonucleotide primer for each different nucleic acid sequence being amplified or detected. If the nucleic acids to be amplified or detected are DNA, then the nucleotide triphosphates are dATP, dCTP, dGTP and TTP.

The nucleic acid strands are used as a template for the synthesis of additional nucleic acid strands. This synthesis can be performed using any suitable method. Generally, it occurs in a buffered aqueous solution, preferably at a pH of 7-9, most preferably about 8. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The resulting solution is then treated according to whether the nucleic acids being amplified or detected are double or single-stranded.

If the nucleic acids are single-stranded, then no denaturation step need be employed, and the reaction mixture is held at a temperature which promotes hybridization of the primer to its complementary target (template) sequence. Such temperature is generally from about 35° to about 65° C. or more, preferably about 37° C. to about 50° C., for an effective time, generally one-half to five minutes, preferably one-three minutes.

The complement to the original single-stranded nucleic acid may be synthesized by adding one or two oligonucleotide primers thereto. If an appropriate single primer is added, a primer extension product is synthesized in the presence of the primer, the thermostable enzyme and the necleotide triphosphates. The product will be partially complementary to the single-stranded nucleic acid and will hybridize with the nucleic acid strand to form a duplex of strands of unequal length which may then be separated into single strands as described above to produce two single separated, complementary strands. Alternatively, two appropriate primers may be added to the single-stranded nucleic acid and the reaction carried out.

If the nucleic acid contains two strands, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90° to 105° C. for times generally ranging from about 0.5 to 5 minutes. Preferably the effective denaturing temperature is 90°-100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology*, 43:63 (1978), and techniques for using RecA are reviewed in C. Radding, Ann. Rev. *Genetics*, 16:405-37 (1982). The denaturation produces two separated complementary strands of equal or unequal length.

If the double-stranded nucleic acid is denatured by heat, the reaction mixture is allowed to cool to a temperature which promotes hybridization of each primer present to its complementary target (template) sequence. This temperature is usually from about 35° to 65° C. or more, preferably from about 37° C. to about 50° C., maintained for an effective time, generally 0.5 to 5 minutes, and preferably 1-3 minutes. In practical terms, the temperature is simply lowered from about 95° C. to about 65° C. or to as low as 37° C. and hybridization occurs at a temperature within this range.

Whether the nucleic acid is single- or double-stranded, the thermostable enzyme may be added at the denaturation step or when the temperature is being reduced to or is in the range for promoting hybridization. The reaction mixture is then heated to a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but not be so high as to denature each extension product from its complementary template (i.e., the temperature is generally less than about 80°-90° C.).

Depending mainly on the types of enzyme and nucleic acid(s) employed, the typical temperature effective for this synthesis reaction generally ranges from about 40° to 80° C., preferably 50°-70° C. The temperature more preferably ranges from about 60°-65° C. when a polymerase from *Thermus aquaticus* is employed. The period of time required for this synthesis may range from about 0.5 to 40 minutes or more, depending mainly on the temperature, the length of the nucleic acid, the enzyme and the complexity of the nucleic acid mixture, preferably 1 to 3 minutes. If the nucleic acid is longer, a longer time period is generally required. Preferably, an amount of dimethylsulfoxide (DMSO) which is sufficient to facilitate detection of amplified product is also present in the reaction mixture. The DMSO may be added at any step of the process herein, but preferably is present at this step and at all succeeding steps. Most preferably, 5-10% by volume of DMSO is present.

The newly synthesized strand and its complementary nucleic acid strand form a double-stranded molecule which is used in the succeeding steps of the process. In the next step, the strands of the double-stranded molecule are separated by heat denaturation at a temperature effective to denature the molecule, but not so high that the thermostable enzyme is completely and irreversibly denatured or inactivated. Depending mainly on the type of enzyme and the length of nucleic acid, this temperature generally ranges from about 90° to 105° C., more preferably 90°-100° C., and the time for denaturation typically ranges from 0.5 to four minutes, depending mainly on the temperature and the nucleic acid length.

After this time, the temperature is decreased to a level which promotes hybridization of the primer to its complementary single-stranded molecule (template) produced from the previous step. Such temperature is described above.

After this hybridization step, or in lieu of (or concurrently with) the hybridization step, the temperature is adjusted to a temperature which is effective to promote the activity of the thermostable enzyme to enable synthesis of a primer extension product using as template the newly synthesized strand from the previous step. The temperature again must not be so high as to separate (denature) the extension product from its template, as previously described (usually from 40° to 80° C. for 0.5 to 40 minutes, preferably 50° to 70° C. for 1-3 minutes). Hybridization may occur during this step, so that the previous step of cooling after denaturation is not required. In such a case using simultaneous steps, a temperature range of 50°-70° C. is preferred.

The heating and cooling steps of strand separation, hybridization, and extension product synthesis can be repeated as often as needed to produce the desired quantity of the specific nucleic acid sequence, depending on the ultimate use. The only limitation is the amount of the primers, the thermostable enzyme and the nucleotide triphosphates present. Preferably, the steps are repeated at least once. For use in detection, the number of cycles will depend, e.g., on the nature of the sample. For example, fewer cycles will be required if the sample being amplified is pure. If the sample is a complex mixture of nucleic acids, more cycles will be required to amplify the signal sufficiently for its detection. For general amplification and detection, preferably the process is repeated at least 20 times.

When labeled sequence-specific probes are employed as described below, preferably the steps are repeated at least five times. When human genomic DNA is employed with such probes, the process is repeated preferably 15-30 times to amplify the sequence sufficiently that a clearly detectable signal is produced, i.e., so that background noise does not interfere with detection.

As will be described in further detail below, the amount of the specific nucleic acid sequence produced will accumulate in an exponential fashion.

No additional nucelotides, primers, or thermostable enzyme need be added after the initial addition, provided that the enzyme has not become denatured or inactivated irreversibly, in which case it is necessary to replenish the enzyme after each denaturing step. Addition of such materials at each step, however, will not adversely affect the reaction.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

After the appropriate length of time has passed to produce the desired amount of the specific nucleic acid sequence, the reaction may be halted by inactivating the enzyme in any known manner or by separating the components of the reaction.

The present invention is demonstrated diagrammatically below, where double-stranded DNA containing the desired sequence [S] comprised of complementary strands [S+] and [S-] is utilized as the nucleic acid.

"long products," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence [S+] or [S-]. These molecules will also function as templates for one or the other of the oligonucleotide primers, producing further [S+] and [S-], and thus a chain reaction can be sustained which will result in the accumulation of [S] at an exponential rate relative to the number of cycles.

By-products formed by oligonucleotide hybridizations other than those intended are not self-catalytic (except in rare instances) and thus accumulate at a linear rate.

The specific sequence to be amplified [S], can be depicted diagrammatically as:

[S+]   5'  AAAAAAAAAAXXXXXXXXXXXCCCCCCCCCC  3'
[S-]   3'  TTTTTTTTTTYYYYYYYYYYGGGGGGGGGG  5'

The appropriate oligonucleotide primers would be:

Primer 1:   GGGGGGGGGG
Primer 2:   AAAAAAAAAA so that if DNA containing [S]

....zzzzzzzzzzzzzzzzAAAAAAAAAAXXXXXXXXXXXCCCCCCCCCCzzzzzzzzzzzzzzzzz....
....zzzzzzzzzzzzzzzzTTTTTTTTTTYYYYYYYYYYGGGGGGGGGGzzzzzzzzzzzzzzzzz....

is separated into single strands and its single strands are hybridized to Primers 1 and 2, the following extension reactions can be catalyzed by a thermostable polymerase in the presence of the four nucleotide triphosphates:

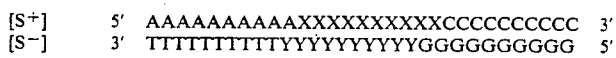

During the first and each subsequent reaction cycle, extension of each oligonucleotide primer on the original template will produce one new ssDNA molecule product of indefinite length which terminates with only one of the primers. These products, hereafter referred to as On denaturation of the two duplexes formed, the products are:

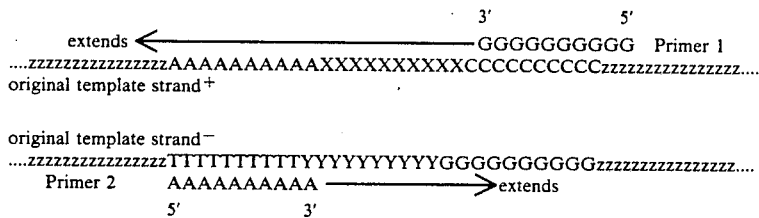

If these four strands are allowed to rehybridize with Primers 1 and 2 in the next cycle, the thermostable polymerase will catalyze the following reactions:

```
Primer 2        5'  AAAAAAAAAA ─────────────────→extends to here
3'....zzzzzzzzzzzzzzzzzzzTTTTTTTTTTTYYYYYYYYYYYGGGGGGGGGG 5'
newly synthesized long product 1 extends ←──────────────── GGGGGGGGGG 5' Primer 1
5'....zzzzzzzzzzzzzzAAAAAAAAAAXXXXXXXXXXCCCCCCCCCCzzzzzzzzzzzzzz....3'
original template strand+

Primer 2        5'  AAAAAAAAAA ─────────────────→extends
3'....zzzzzzzzzzzzzzzzzzTTTTTTTTTTTYYYYYYYYYYYGGGGGGGGGGzzzzzzzzzz....5'
original template strand− extends to here ←──────────── GGGGGGGGGG 5' Primer 1

5' AAAAAAAAAAXXXXXXXXXXCCCCCCCCCCzzzzzzzzzzzzzzzz..3'
        newly synthesized long product 2
```

If the strands of the above four duplexes are separated, the following strands are found:

```
        5' AAAAAAAAAAXXXXXXXXXXCCCCCCCCCC 3'
        newly synthesized [S+]

3'....zzzzzzzzzzzzzzzzzzzTTTTTTTTTTTYYYYYYYYYYYGGGGGGGGGG 5'
first cycle synthesized long product 1

3'....zzzzzzzzzzzzzzzzzzzTTTTTTTTTTTYYYYYYYYYYYGGGGGGGGGG 5'
newly synthesized long product 1

5'....zzzzzzzzzzzzzzzzzAAAAAAAAAAXXXXXXXXXXCCCCCCCCCCzzzzzzzzzz....3'
original template strand+

5' AAAAAAAAAAXXXXXXXXXXCCCCCCCCCCzzzzzzzzzzzzzzzz...3'
        newly synthesized long product 2

3'..zzzzzzzzzzzzzTTTTTTTTTTTYYYYYYYYYYYGGGGGGGGGGzzzzzzzzzzzzzzzz...5'
original template strand−

3' TTTTTTTTTTTYYYYYYYYYYYGGGGGGGGGG 5'
        newly synthesized [S−]

5' AAAAAAAAAAXXXXXXXXXXCCCCCCCCCCzzzzzzzzzzzzzz...3'
        first cycle synthesized long product 2
```

It is seen that each strand which terminates with the oligonucleotide sequence of one primer and the complementary sequence of the other is the specific nucleic acid sequence [S]] that is desired to be produced.

The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

| | Number of Double Strands After 0 to n Cycles | | |
|---|---|---|---|
| Cycle Number | Template | Long Products | Specific Sequence [S] |
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |

| | Number of Double Strands After 0 to n Cycles | | |
|---|---|---|---|
| Cycle Number | Template | Long Products | Specific Sequence [S] |
| n | 1 | n | $(2^n - n - 1)$ |

When a single-stranded nucleic acid is utilized as the template, only one long product is performed per cycle.

A sequence within a given sequence can be amplified after a given number of amplifications to obtain greater specificity of the reaction by adding after at least one cycle of amplification a set of primers which are complementary to internal sequences (which are not on the ends) of the sequence to be amplified. Such primers may be added at any stage and will provide a shorter amplified fragment. Alternatively, a longer fragment can be prepared by using primers with non-complementary ends but having some overlap with the primers previously utilized in the amplification.

The amplification method may be utilized to clone a particular nucleic acid sequence for insertion into a suitable expression vector. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers.

In addition, the amplification process an be used for in vitro mutagenesis. The oligodeoxybribonucleotide primers need not be exactly complementary to the DNA sequence which is being amplified. It is only necessary that they be able to hybridize to the sequence sufficiently well to extended by the thermostable enzyme. The product of an amplification reaction wherein the primers employed are not exactly complementary to the original template will contain the sequence of the primer rather than the template, thereby introducing an in vitro mutation. In further cycles this mutation will be amplified with an undiminished efficiency because no further mispaired priming are required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers to induce further sequence changes. In this way, a series of mutated sequences could gradually be produced wherein each new addition to the series could differ from the last in a minor way, but from the original DNA source sequence in an increasingly major way. In this manner, changes could be made ultimately which were not feasible in a single step due to the inability of a very seriously mismatched primer to function.

In addition, the primer can contain as part of its sequence a non-complementary sequence, provided that a sufficient amount of the primer contains a sequence which is complementary to the strand to be amplified. For example, a nucleotide sequence which is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

The amplification method may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells. Amplification is particularly useful if such an analysis is to be done on a small sample using non-radioactive detection techniques which may be inherently insensitive, or where radioactive techniques are being employed, but where rapid detection is desirable.

For the purposes of this discussion, genetic diseases may include specific deletions and/or mutations in genomic DNA from any organism, such as, e.g., sickle cell anemia, α-thalassemia, β-thalassemia, and the like. Sickle cell anemia can be readily detected via oligomer restriction analysis as described by EP Patent Publication 164,054 published Dec. 11, 1985, or via a RFLP-like analysis following amplification of the appropriate DNA sequence by the amplification method. α-Thalassemia can be detected by the absence of a sequence, and β-thalassemia can be detected by the presence of a polymorphic restriction site closely linked to a mutation that causes the disease.

All of these genetic diseases may be detected by amplifying the appropriate sequence and analyzing it by Southern blots without using radioactive probes. In such a process, for example, a small sample of DNA from, e.g., amniotic fluid containing a very low level of the desired sequence is amplified, cut with a restriction enzyme, and analyzed via a Southern blotting technique. The use of non-radioactive probes is facilitated by the high level of the amplified signal.

In another embodiment, a small sample of DNA may be amplified to a convenient level and then a further cycle of extension reactions performed wherein nucleotide derivatives which are readily detectable (such as $^{32}P$-labeled or biotin-labeled nucleotide triphosphates) are incorporated directly into the final DNA product, which may be analyzed by restriction and electrophoretic separation or any other appropriate method.

In a further embodiment, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

A practical application of the amplification technique, that is, in facilitating the detection of sickle cell anemia via the oligomer restriction technique [described in EP 164,054, supra, and by Saiki et al., Bio/Technology, Vol. 3, pp. 1008-1012 (1985)] is describe in detail in the Saiki et al. Science article cited above. In that Science article, a specific amplification protocol is exemplified using a β-globin gene segment.

The amplification method herein may also be used to detect directly single-nucleotide variations in nucleic acid sequence (such as genomic DNA) using sequence-specific oligonucleotides, as described more fully in copending U.S. Ser. No. 839,331 filed Mar. 13, 1986 and in copending U.S. Ser. No. Cetus Case 2262.1 filed concurrently herewith, which is a continuation-in-part of U.S. Ser. No. 839,331, the disclosures of both of which are incorporated herein by reference.

Briefly, in this process, the amplified sample is spotted directly on a series of membranes, and each membrane is hybridized with a different labeled sequence-specific oligonucleotide probe. After hybridization the sample is washed and the label is detected. This technique is especially useful in detecting DNA polymorphisms.

Various infectious diseases can be diagnosed by the presence in clinical samples of specific DNA sequences characteristic of the causative microorganism. These include bacteria, such as Salmonella, Chlamydia, Neisseria; viruses, such as the hepatitis viruses, and parasites, such as the Plasmodium responsible for malaria. U.S. Pat. Reexamination Certificate B1 4,358,535 issued to Falkow et al. on May 13, 1986 describes the use of specific DNA hybridization probes for the diagnosis of infectious diseases. A relatively small number of pathogenic organisms may be present in a clinical sample from an infected patient and the DNA extracted from these may constitute only a very small fraction of the total DNA in the sample. Specific amplification of suspected sequences prior to immobilization and detection by hybridization of the DNA samples could greatly improve the sensitivity and specificity of traditional procedures.

Routine clinical use of DNA probes for the diagnosis of infectious diseases would be simplified considerably if non-radioactively labeled probes could be employed as described in EP 63,879 to Ward. In this procedure biotin-containing DNA probes are detected by chromogenic enzymes linked to avidin or biotin-specific antibodies. This type of detection is convenient, but relatively insensitive. The combination of specific DNA amplification by the present method and the use of stably labeled probes could provide the convenience and sensitivity required to make the Falkow et al. and Ward procedures useful in a routine clinical setting.

A specific use of the amplification technology for detecting or monitoring for the AIDS virus is described in copending U.S. application Ser. No. 818,127, filed Jan. 10, 1986, the disclosure of which is incorporated herein by reference. Briefly, the amplification and detection process is used with primers and probes which are designed to amplify and detect, respectively, nucleic acid sequences which are substantially conserved among the nucleic acids in AIDS viruses and specific to the nucleic acids in AIDS viruses. Thus, the sequence to be detected must be sufficiently complementary to the nucleic acids in AIDS viruses to initiate polymerization preferably at room temperature in the presence of the enzyme and nucleotide triphosphates.

The amplification process can also be utilized to produce sufficient quantities of DNA from a single copy human gene such that detection by a simple non-specific DNA strain such as ethidium bromide can be employed to diagnose DNA directly.

In addition to detecting infectious diseases and pathological abnormalities in the genome of organisms, the amplification process can also be used to detect DNA polymorphisms which may not be associated with any pathological state.

In summary, the amplification process is seen to provide a process for amplifying one or more specific nucleic acid sequences using a chain reaction and a thermostable enzyme, in which reaction primer extension products are produced which can subsequently act a templates for further primer extension reactions. The process is especially useful in detecting nucleic acid sequences which are initially present in only very small amounts.

The following examples are offered by way of illustration only and are by no means intended to limit the scope of the claimed invention. In these samples, all percentages are by weight if for solid and by volume if for liquids, and all temperatures are given in degrees Celsius.

EXAMPLE I

I. Synthesis of the Primers

The following two oligonucleotide primers were prepared by the method described below:

5'-ACACAACTGTGTCACTAGC-3'  (PC03)
5'-CAACTTCATCCACGTTCACC-3'  (PC04)

These primers, both 20-mers, anneal to opposite strands of the genomic DNA with their 5' ends separated by a distance of 110 base pairs.

A. Automated Synthesis Procedures: The diethylphosphoramidites, synthesized according to Beaucage and Caruthers (*Tetrahedron Letters* (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine in tetrahydrofuran and pyridine. Cycle time was approximately 30 minutes. Yields at each step were essentially quantitative and were determined by collection and spectroscopic examination of the dimethoxytrityl alcohol released during detritylation.

B. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of Oligodeoxyribonucleotides: Test aliquots of the purified oligonucleotides were $^{32}P$ labeled with polynucleotide kinase and $\gamma\text{-}^{32}P\text{-ATP}$. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

II. Isolation of Human Genomic DNA from Cell Line

High molecular weight genomic DNA was isolated from a T cell line, Molt 4, homozygous for normal β-globin available from the Human Genetic Mutant Cell Depository, Camden, N.J. as GM2219C using essentially the method of Maniatis et al., *Molecular Cloning* (1982), 280–281.

III. Purification of a Polymerase From *Thermus aquaticus*

*Thermus aquaticus* strain YT1, available without restriction from the American Type Culture Collection, 12301 Parklawn Drive, Rockville, Md., as ATCC No. 25,104 was grown in flasks in the following medium:

| | |
|---|---|
| Sodium Citrate | 1 mM |
| Potassium Phosphate, pH 7.9 | 5 mM |
| Ammonium Chloride | 10 mM |
| Magnesium Sulfate | 0.2 mM |
| Calcium Chloride | 0.1 mM |

-continued

| Sodium Chloride | 1 g/l |
| --- | --- |
| Yeast Extract | 1 g/l |
| Tryptone | 1 g/l |
| Glucose | 2 g/l |
| Ferrous Sulfate | 0.01 mM |

(the pH was adjusted to 8.0 prior to autoclaving.)

A 10-liter fermentor was inoculated from a seed flask cultured overnight in the above medium at 70° C. A total of 600 ml from the seed flask was used to inoculate 10 liters of the same medium. The pH was controlled at 8.0 with ammonium hydroxide with the dissolved oxygen at 40%, with the temperature at 70° C., and with the stirring rate at 400 rpm.

After growth of the cells, they were purified using the protocol (with slight modification) of Kaledin et al., supra, through the first five stages and using a different protocol for the sixth stage. All six steps were conducted at 4° C. The rate of fractionation on columns was 0.5 column volumes/hour and the volumes of gradients during elution were 10 column volumes.

Briefly, the above culture of the *T. aquaticus* cells was harvested by centrifugation after nine hours of cultivation, in late log phase, at a cell density of 1.4 g dry weight/l. Twenty grams of cells was resuspended in 80 ml of a buffer consisting of 50 mM Tris·HCl pH 7.5, 0.1 mM EDTA. Cells were lysed and the lysate was centrifuged for two hours at 35,000 rpm in a Beckman TI 45 rotor at 4° C. The supernatant was collected (fraction A) and the protein fraction precipitating between 45 and 75% saturation of ammonium sulfate was collected, dissolved in a buffer consisting of 0.2M potassium phosphate buffer, pH 6.5, 10 mM 2-mercaptoethanol, and 5% glycerine, and finally dialyzed against the same buffer to yield fraction B.

Fraction B was applied to a 2.2×30-cm column of DEAE-cellulose, equilibrated with the above described buffer. The column was then washed with the same buffer and the fractions containing protein (determined by absorbance at 280 nm) were collected. The combined protein fraction was dialyzed against a second buffer, containing 0.01M potassium phosphate buffer, pH 7.5, 10 mM 2-mercaptoethanol, and 5% glycerine, to yield fraction C.

Fraction C was applied to a 2.6×21-cm column of hydroxyapatite, equilibrated with a second buffer. The column was then washed and the enzyme was eluted with a linear gradient of 0.01–0.5M potassium phosphate buffer, pH 7.5, containing 10 mM 2-mercaptoethanol and 5% glycerine. Fractions containing DNA polymerase activity (90–180 mM potassium phosphate) were combined, concentrated four-fold using an Amicon stirred cell and YM10 membrane, and dialyzed against the second buffer to yield fraction D.

Fraction D was applied to a 1.6×28-cm column of DEAE-cellulose, equilibrated with the second buffer. The column was washed and the polymerase was eluted with a linear gradient of 0.01–0.5M potassium phosphate in the second buffer. The fractions were assayed for contaminating endonuclease(s) and exonuclease(s) by electrophoretically detecting the change in molecular weight of phage λ DNA or supercoiled plasma DNA after incubation with an excess of DNA polymease (for endonuclease) and after treatment with a restriction enzyme that cleaves the DNA into several fragments (for exonuclease). Only those DNA polymerase fractions (65–95 mM potassium phosphate) having minimal nuclease contamination were pooled. To the pool was added autoclaved gelatin in an amount of 250 μg/ml, and dialysis was conducted against the second buffer to yield Fraction E.

Fraction E was applied to a 9 ml phosphocellulose column and eluted with a 100 ml gradient (0.01–0.4M KCl gradient in 20 mM potassium phosphate buffer pH 7.5). The fractions were assayed for contaminating endo/exonuclease(s) as described above as well as for polymerase activity (by the method of Kaledin et al.) and then pooled. The pooled fractions were dialyzed against the second buffer, then concentrated by dialysis against 50% glycerine and the second buffer.

The molecular weight of the polymerase was determined by SDS PAGE. Marker proteins (bio-Rad low molecular weight standards) were phosphorylase B (92,500), bovine serum albumin (66,200), ovalbumin (45,000), carbonic anhydrase (31,000), soybean trypsin inhibitor (21,500), and lysozyme (14,400).

Preliminary data suggest that the polymerase has a molecular weight of about 86,000–90,000 daltons, not 62,000–63,000 daltons reported in the literature (e.g., by Kaledin et al.).

IV. Amplification Reaction

One microgram of the genomic DNA described above was diluted in an initial 100 μl aqueous reaction volume containing 25 mM Tris·HCl buffer (pH 8.0), 50 mM KCl, 10 mM MgCl$_2$, 5 mM dithiothreitol, 200 μg/ml gelatin, 1 μM of primer PC03, 1 μM of primer PC04, 1.5 mM dATP, 1.5 mM dCTP, 1.5 mM dGTP and 1.5 mM TTP. The sample was heated for 10 minutes at 98° C. to denature the genomic DNA, then cooled to room temperature. Four microliters of the polymerase from *Thermus aquaticus* was added to the reaction mixture and overlaid with a 100 μl mineral oil cap. The sample was then placed in the aluminum heating block of the liquid handling and heating instrument described in copending U.S. application Ser. No. 833,368 filed Feb. 25, 1986, the disclosure of which is incorporated herein by reference.

The DNA sample underwent 20 cycles of amplification in the machine, repeating the following program cycle:

1) heating from 37° C. to 98° C. in heating block over a period of 2.5 minutes; and 2) cooling from 98° C. to 37° C. over a period of three minutes to allow the primers and DNA to anneal.

After the last cycle, the sample was incubated for an additional 10 minutes at 55° C. to complete the final extension reaction.

V. Synthesis and Phosphorylation of Oligodeoxyribonucleotide Probes

A labeled DNA probe, designated RS24, of the following sequence was prepared:

5'-*CCCACAGGGCAGTAACG-
GCAGACTTCTCCTCAGGAGTCAG-3'
(RS24)

where * indicates the label. This probe is 40 bases long, spans the fourth through seventeenth codons of the gene, and is complementary to the normal β-globin allele (β$^A$). The schematic diagram of primers and probes is given below:

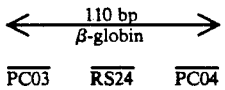

This probe was synthesized according to the procedures described in Section I of Example I. The probe was labeled by contacting 20 pmole thereof with 4 units of T4 polynucleotide kinase (New England Biolabs) and about 40 pmole $\gamma\text{-}^{32}P$-ATP (New England Nuclear, about 7000 Ci/mmole) in a 40 µl reaction volume containing 70 mM tris buffer (pH 7.6), 10 mM MgCl$_2$, 1.5 mM spermine and 10 mM dithiothreitol for 60 minutes at 37° C. The total volume was then adjusted to 100 µl with 25 mM EDTA and purified according to the procedure of Maniatis et al., *Molecular Cloning* (1982), 446–467 over a 1 ml Bio Gel P-4 (Bio-Rad) spin dialysis column equilibrated with Tris-EDTA (TE) buffer (10 mM tris buffer, 0.1 mM EDTA, pH 8.0). TCA precipitation of the reaction product indicated that for RS24 the specific activity was 4.3 µCi/pmole and the final concentration was 0.118 pmole/µl.

VI. Dot Blot Hybridizations

Four microliters of the amplified sample from Section I and 5.6 µl of appropriate dilutions of β-globin plasmid DNA calculated to represent amplification efficiencies of 70, 75, 80, 85, 90, 95 and 100% were diluted with 200 µl 0.4N NaOH, 25 mM EDTA and spotted onto a Genatran 45 (Plasco) nylon filter by first wetting the filter with water, placing it in a Bio-Dot (Bio-Rad, Richmond, Calif.) apparatus for preparing dot blots which holds the filters in place, applying the samples, and rinsing each well with 0.1 ml of 20×SSPE (3.6M NaCl, 200 mM NaH$_2$PO$_4$, 20 mM EDTA), as disclosed by Reed and Mann, *Nucleic Acids Research,* 13, 7202–7221 (1985). The filters were then removed rinsed in 20×SSPE, and baked for 30 minutes at 8020 C. in a vacuum oven.

After baking, each filter was then contacted with 16 ml of a hybridization solution consisting of 3×SSPE, 5×Denhardt's solution (133=0.02% polyvinylpyrrolidone, 0.02% Ficoll, 0.02% bovine serum albumin, 0.2 mM Tris, 0.2 mM EDTA, pH 8.0), 0.5% SDS, and 30% formamide, and incubated for two hours at 42° C. Then 2 pmole of probe RS24 was added to the hybridization solution and the filter was incubated for two hours at 42° C.

Finally, each hybridized filter was washed twice with 100 ml of 2×SSPE and 0.1% SDS for 10 minutes at room temperature. Then the filters were treated once with 100 ml of 2×SSPE, 0.1% SDS at 60° C. for 10 minutes.

Each filter was then autoradiographed, with the signal readily apparent after two hours.

VII. Discussion of Autoradiogram

The autoradiogram of the dot blots was analyzed after two hours and compared in intensity to standard serial dilution β-globin reconstructions prepared with HaeIII/MaeI-digested pBR:β$^A$, where β$^A$ is the wild-type allele, as described in Saiki et al., *Science,* supra. Analysis of the reaction product indicated that the overall amplification efficiency was about 95%, corresponding to a 630,000-fold increase in the β-globin target sequence.

EXAMPLE II

I. Amplification Reaction

Two 1 µg samples of genomic DNA extracted from the Molt 4 cell line as described in Example I were each diluted in a 100 µl reaction volume containing 50 mM KCl, 25 mM Tris·HCl buffer pH 8.0, 10 mM MgCl$_2$, 1 µM of primer PCO3, 1 µM of primer PC04, 200 µg/ml gelatin, 10% dimethylsulfoxide (by volume), 1.5 mM dATP, 1.5 mM dCTP, 1.5 mM dGTP, and 1.5 mM TTP. After this mixture was heated for 10 minutes at 98° C. to denature the genomic DNA, the samples were cooled to room temperature and 4 µl of the polymerase from *Thermus aquaticus* described in Example I was added to each sample. The samples were overlaid with mineral oil to prevent condensation and evaporative loss.

One of the samples was placed in the heating block of the machine described in Example I and subjected to 25 cycles of amplification, repeating the following program cycle:

(1) heating from 37° to 93° C. over a period of 2.5 minutes;

(2) cooling from 93° C. to 37° C. over a period of three minutes to allow the primers and DNA to anneal; and (3) maintaining at 37° C. for two minutes.

After the last cycle the sample was incubated for an additional 10 minutes at 60° C. to complete the final extension reaction.

The second sample was placed in the heat-conducting container of the machine, described in more detail in copending U.S. Ser. No. Cetus Case 2264.1 filed concurrently herewith, supra. The heat-conducting container is attached to Peltier heat pumps which adjust the temperature upwards or downwards and a microprocessor controller to control automatically the amplification sequence, the temperature levels, the temperature ramping and the timing of the temperature.

The second sample was subjected to 25 cycles of amplification, repeating the following program cycle:

(1) heating from 37° to 95° C. over a period of three minutes;

(2) maintaining at 95° C. for 0.5 minutes to allow denaturation to occur;

(3) cooling from 95° to 37° C. over a period of one minute; and (4) maintaining at 37° for one minute.

II. Analysis

Two tests were done for analysis, a dot blot and an agarose gel analysis.

For the dot blot analysis, a labeled DNA probe, designated RS18, of the following sequence was prepared.

5'-*CTCCTGAGGAGAAGTCTGC-3' (RS18)

where * indicates the label. This probe is 19 bases long, spans the fourth through seventeenth codons of the gene, and is complementary to the normal β-globin allele (β$^A$). The schematic diagram of primers and probes is given below:

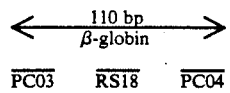

This probe was synthesized according to the procedures described in Section I of Example I. The probe was labeled by contacting 10 pmole thereof with 4 units of T4 polynucleotide kinase (New England Biolabs) and about 40 pmole $\lambda$-$^{32}$P-ATP (New England Nuclear, about 7000 Ci/mmole) in a 40 µl reaction volume containing 70 mM Tris·HCl buffer (pH 7.6), 10 mM MgCl$_2$, 1.5 mM spermine and 10 mM dithiothreitol for 60 minutes at 37° C. The total volume was then adjusted to 100 µl with 25 mM EDTA and purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris·HCl buffer, 0.1 mM EDTA, pH 8.0). TCA precipitation of the reaction product indicated that for RS18 the specific activity was 4.6 µCi/pmole and the final concentration was 0.114 pmole/µl.

Five microliters of the amplified sample from Section I and of a sample amplified as described above except using the Klenow fragment of *E. coli* DNA Polymerase I instead of the thermostable enzyme were diluted with 195 µl 0.4N NaOH, 25 mM EDTA and spotted onto two replicate Genatran 45 (Plasco) nylon filters by first wetting the filters with water, placing them in a Bio-Dot (Bio-Rad, Richmond, Calif.) apparatus for preparing dot blots which holds the filters in place, applying the samples, and rinsing each well with 0.4 ml of 20×SSPE (3.6M NaCl, 200 mM NaH$_2$PO$_4$, 20 mM EDTA), as disclosed by Reed and Mann, *Nucleic Acids Research*, 13, 7202–7221 (1985). The filters were then removed, rinsed in 20×SSPE, and baked for 30 minutes at 80° C. in a vacuum oven.

After baking, each filter was then contacted with 6 ml of a hybridization solution consisting of 5×SSPE, 5×Denhardt's solution (1× =0.02% polyvinylpyrrolidone, 0.02% Ficoll, 0.02% bovine serum albumin, 0.2 mM Tris, 0.2 mM EDTA, pH 8.0) and 0.5% SDS, and incubated for 60 minutes at 55° C. Then 5 µl of probe RS18 was added to the hybridization solution and the filter was incubated for 60 minutes at 55° C.

Finally, each hybridized filter was washed twice with 100 ml of 2×SSPE and 0.1% SDS for 10 minutes at room temperature. Then the filters were treated twice more with 100 ml of 5×SSPE, 0.1% SDS at 60° C. for 1) one minute and 2) three minutes, respectively.

Each filter was then autoradiographed, with the signal readily apparent after 90 minutes.

In the agarose gel analysis, 5 µl each amplification reaction was loaded onto 4% NuSieve/0.5% agarose gel in 1×TBE buffer (0.089M Tris borate, 0.089M boric acid, and 2 mM EDTA) and electrophoresed for 60 minutes at 100V. After staining with ethidium bromide, DNA was visualized by UV fluorescence.

The results show that the machines used in Example I and this example herein were equally effective in amplifying the DNA, showing discrete high-intensity 110-base pair bands of similar intensity, corresponding to the desired sequence, as well as a few other discrete bands of much lower intensity. In contrast, the amplification method as described in Example I of copending U.S. application Ser. No. 839,331 filed Mar. 13, 1986, supra, which involves reagent transfer after each cycle using the Klenow fragment of *E. coli* Polymerase I, gave a DNA smear resulting from the non-specific amplification of many unrelated DNA sequences.

It is expected that similar improvements in amplification and detection would be achieved in evaluating HLA-DQ, DR and DP regions.

EXAMPLE III

Amplification and Cloning

For amplification of a 119-base pair fragment on the human β-hemoglobin gene, a total of 1 microgram each of human genomic DNA isolated from the Molt 4 cell line or from the GM2064 cell line (representing a homozygous deletion of the β- and Δ- hemoglobin region and available from the Human Genetic Mutant Cell Depository, Camden, N.J.) as described above was amplified in a 100 µl reaction volume containing 50 mM KCl, 25 mM Tris·HCl pH 8, 10 mM MgCl$_2$, 200 µg/ml gelatin, 5 mM beta-mercaptoethanol, 1.5 mM dATP, 1.5 mM dCTP, 1.5 mM dTTP, 1.5 mM dGTP, and 1 µM of each of the following primers:

```
5'-CTTCTGcagCAACTGTGTTCACTAGC-3'   (GH18)
5'-CACaAgCTTCATCCACGTTCACC-3'      (GH19)
``` where lower case letters denote mismatches from wild-type sequence to create restriction enzyme sites. GH18 is a 26-base oligonucleotide complementary to the negative strand and contains an internal PstI site. GH19 is a 23-base oligonucleotide complementary to the plus strand and contains an internal HindIII recognition sequence. These primers were selected by first screening the regions of the gene for homology to the PstI and HindIII restriction sites of bacteriophage M13. The primers were then prepared as described in Example I.

The above reaction mixtures were heated for 10 minutes at 95° C. and then cooled to room temperature. A total of 4 µl of the polymerase described in Example I was added to each reaction mixture, and then each mixture was overlayed with mineral oil. The reaction mixtures were subjected to 30 cycles of amplification with the following program:

2.5 min. ramp, 37° to 98° C.
.3 min. ramp, 98° to 37° C.
2 min. soak, 37° C.

After the last cycle, the reaction mixtures were incubated for 20 minutes at 65° C. to complete the final extension. The mineral oil was extracted with chloroform and the mixtures were stored at 20° C.

A total of 10 µl of the amplified product was digested with 0.5 µg M13mp10 cloning vector, which is publicly available from Boehringer-Mannheim in a 50 µvolume containing 50 mM NaCl, 10 mM Tris·HCl, pH 7.8, 10 mM MgCl$_2$, 20 units PstI and 26 units HindIII for 90 minutes at 37° C. The reaction was stopped by freezing at 20° C. The volume was adjusted to 110 µl with TE buffer and loaded (100 µl) onto a 1 ml BioGel P-4 spin dialysis column. One 0.1 ml fraction was collected and ethanol precipitated.

(At this point it was discovered that there was β-globin amplification product in the GM2064 sample. Subsequent experiments traced the source of contamination to the primers, either GH18 or GH19. Because no other source of primers was available, the experiment was continued with the understanding that some cloned sequences would be derived from the contaminating DNA in the primers.)

The ethanol pellet was resuspended in 15 µl water, then adjusted to 20 µl volume containing 50 mM Tris·HCl, pH 7.8, 10 mM MgCl$_2$, 0.5 mM ATP, 10 mM dithiothreitol, and 400 units ligase. This mixture was incubated for three hours at 16° C.

Ten microliters of ligation reaction mixture containing Molt 4 DNA was transformed into *E. coli* strain JM103 competent cells, which are publicly available from BRL in Bethesda, Md. The procedure followed for preparing the transformed strain is described in Messing, J. (1981) *Third Cleveland Symposium on Macromolecules:Recombinant DNA*, ed. A. Walton, Elsevier, Amsterdam, 143-153. A total of 651 colorless plaques (and 0 blue plaques) were obtained. Of these, 119 had a (+)-strand insert (18%) and 19 had a (−)-strand insert (3%). This is an increase of almost 20-fold over the percentage of β-globin positive plaques among the primer-positive plaques from the amplification technique using Klenow fragment of *E. coli* Polymerase I, where the reaction proceeded for two minutes at 25° C., after which the steps of heating to 100° C. for two minutes, cooling, adding Klenow fragment, and reacting were repeated nine times. These results confirm the improved specificity of the amplification reaction employing the thermostable enzyme herein.

In a later cloning experiment with GM2064 and the contaminated primers, 43 out of 510 colorless plaques (8%) had the (+)-strand insert. This suggests that approximately one-half of the 119 clones from Molt 4 contain the contaminant sequence.

Ten of the (+)-strand clones from Molt 4 were sequenced. Five were normal wild-type sequence and five had a single C to T mutation in the third position of the second codon of the gene (CAC to CAT). Four of the contaminant clones from GM2064 were sequenced and all four were normal.

Restriction site-modified primers may also be used to amplify and clone and partially sequence the human N-ras oncogene and to clone base pair segments of the HLA DQ-α, DQ-β and DR-β genes using the above technique. All of these amplification reactions may be carried out in the presence of 10% by volume dimethylsulfoxide.

Plating and Screening

The filters were probed with the primer PC04 to determine the percentage of inserts resulting from amplification and cloning. The percentage of β-globin positive plaques among the amplified primer-positive plaques was approximately 20%. This is an increase of 20-fold over the percentage of β-globin positive plaques among the primer-positive plaques from the amplification technique using Klenow fragment of *E. coli* Polymerase I, where the reaction proceeded for two minutes at 25° C., after which the steps of heating to 100° C. for two minutes, cooling, adding Klenow fragment, and reacting were repeated nine times. These results confirm the improved specificity of the amplification reaction of the invention herein employing a thermostable enzyme.

Restriction site-modified primers may also be used to amplify and clone and partially sequence the human N-ras oncogene and to clone base pair segments of the HLA DQ-α, DQ-β, and DR-β genes using the above technique. All of these amplification reactions may be carried out in the presence of 10% by volume dimethylsulfoxide.

In summary, the present invention provides an apparatus for performing automated amplification of one or more nucleic acid sequences involving a temperature-cycled chain reaction and a thermostable enzyme, which apparatus has a heat-conducting container for the reagents, means for heating, cooling and maintaining the container to or at any given temperature, and a computer means to generate signals that control the temperature levels. The amplification process results in increased yield of amplified product, greater specificity, and fewer steps necessary to carry out the procedure over what has been previously disclosed.

Other modifications of the above-described embodiments of the invention that are obvious to those of skill in the mechanical and electrical arts and related disciplines are intended to be within the scope of the following claims.

What is claimed is:

1. An apparatus for performing temperature cycling of a reaction mix comprising:
   a heat-conducting container for holding a reaction mixture;
   means for heating and cooling said container to or at any of a plurality of user-defined temperatures and having a control input for receiving a control signal controlling whether said container is heated or cooled; and
   a computer means, coupled to said control input of said means, for receiving and storing checkpoint data from the user defining the plurality of temperatures and the times at which said temperatures are to be attained thereby defining a temperature profile, and for, upon receipt of a command from the user, accessing said checkpoint data and generating control signals therefrom at the control input of said means for heating and cooling to cause the user-defined temperature profile to be achieved at said container; and
   wherein said means for heating and cooling is an aluminum plate having fluid flow channels formed therein which are in fluid communication with pumps which circulate fluid stored in fluid reservoirs having heating and cooling elements therein to keep the fluid at a constant, user-definable temperature.

2. An apparatus for performing temperature cycling of a reaction mix comprising:
   a heat-conducting container for holding a reaction mixture;
   means for heating and cooling said container to or at any of a plurality of user-defined temperatures and having a control input for receiving a control signal controlling whether said container is heated or cooled; and
   a computer means, coupled to said control input of said means, for receiving and storing checkpoint data from the user defining the plurality of temperatures and the times at which said temperatures are to be attained thereby defining a temperature profile, and for, upon receipt of a command from the user, accessing said checkpoint data and generating control signals therefrom at the control input of said means for heating and cooling to cause the user-defined temperature profile to be achieved at said container; and
   wherein said computer means includes means for receiving and storing in a link data field in a database associated with each said temperature profile stored by said computer means link data entered by the user for every set of checkpoints defining a temperature profile, and for receiving and storing a plurality of sets of checkpoints input by the user to define a plurality of temperature profiles, each of which has its own link data item, and wherein said computer means also includes means to run any particular temperature profile identified, if any is identified, in the link data field of the temperature profile just run and to continue this process of running the temperature profiles identified in the link data fields associated with each temperature profile run until no more temperature profiles are identified.

3. An apparatus for performing temperature cycling of a reaction mix comprising:
   a heat-conducting container for holding a reaction mixture;
   means for heating and cooling said container to or at any of a plurality of user-defined temperatures and having a control input for receiving a control signal controlling whether said container is heated or cooled; and
   a computer means, coupled to said control input of said means, for receiving and storing checkpoint data from the user defining the plurality of temperatures and the times at which said temperatures are to be attained thereby defining a temperature profile, and for, upon receipt of a command from the user, accessing said checkpoint data and generating control signals therefrom at the control input of said means for heating and cooling to cause the user-defined temperature profile to be achieved at said container; and
   wherein said computer means includes means for receiving and storing in a link data field in a database associated with each said temperature profile stored by said computer means link data entered by the user for every set of checkpoints defining a temperature profile, and for receiving and storing a plurality of sets of checkpoints input by the user to define a plurality of temperature profiles, each of which has its own link data item, and wherein said computer means also includes means to run any particular temperature profile identified, if any is identified, in the link data field of the temperature profile just run and to continue this process of running the temperature profiles identified in the link data fields associated with each temperature profile run until no more temperature profiles are identified; and
   further comprising means in said computer means for receiving and storing data for a number of cycles data field from the user for each set of checkpoints entered by the user to define a temperature profile and for running each temperature profile the number of times identified in said number of cycles data field before checking said link field of the temperature profile for the identification of the temperature profile to be run next.

4. An apparatus for performing automated amplification of at least one specific nucleic acid sequence comprising:
   a first means for holding a reaction mixture comprising said nucleic acid sequence(s) to be amplified, four different nucleotide triphosphates, a thermostable enzyme, and one oligonucleotide primer for each different specific sequence being amplified, wherein each primer is selected to be substantially complementary to different strands of each specific sequence, such that the extension product synthesized from one primer, when it is separated from its complement, can serve as a template for synthesis of the extension product of the other primer, said holding being carried out at any selected temperature or plurality of temperatures; and
   a second means for automatically performing a predetermined sequence of steps including causing said first means to heat its contents for a first period and to cool its contents for a second period; and
   wherein said second means includes means for allowing the user to enter data which control certain process parameters that characterize predetermined steps in said sequence of steps; and
   wherein said first means holds said liquid stored therein at either of two temperatures and wherein said second second means causes said first means to hold its contents at a first temperature for a user-defined interval followed by a chill-down period and a low-temperature incubation at said second temperature having a user-defined duration; and
   wherein said first means is a reaction chamber thermally coupled to an aluminum plate having fluid flow channels formed therein which are in fluid communication with pumps which circulate fluid stored in fluid reservoirs having heating and cooling elements therein to keep the fluid at a constant, user-definable temperature.

* * * * *